US007049481B1

(12) United States Patent
Chiang et al.

(10) Patent No.: US 7,049,481 B1
(45) Date of Patent: May 23, 2006

(54) CELLULOSE SYNTHASE ENCODING POLYNUCLEOTIDES AND USES THEREOF

(75) Inventors: Vincent L. Chiang, Hancock, MI (US); Luguang Wu, Kenmore (AU); Chandrashekhar P. Joshi, Houghton, MI (US); Daniel T. Carraway, Bainbridge, GA (US)

(73) Assignee: Board of Control of Michigan Technological University, Houghton, MI (US)

( * ) Notice: Subject to any disclaimer, the term of this patent is extended or adjusted under 35 U.S.C. 154(b) by 0 days.

(21) Appl. No.: 09/980,043

(22) PCT Filed: May 18, 2000

(86) PCT No.: PCT/US00/13637

§ 371 (c)(1),
(2), (4) Date: Apr. 5, 2002

(87) PCT Pub. No.: WO00/71670

PCT Pub. Date: Nov. 30, 2000

Related U.S. Application Data

(60) Provisional application No. 60/135,280, filed on May 21, 1999.

(51) Int. Cl.
*C12N 15/09* (2006.01)
*C12N 15/29* (2006.01)
*C12N 15/82* (2006.01)
*A01H 5/00* (2006.01)
*A01H 5/10* (2006.01)

(52) U.S. Cl. ............ 800/278; 800/298; 800/295; 435/320.1; 435/468; 536/23.2; 536/23.6

(58) Field of Classification Search .......... 800/290, 800/298, 278, 286, 287, 295; 435/69.1, 320.1, 435/419, 468; 536/23.2, 23.6, 24.5, 24.4
See application file for complete search history.

(56) References Cited

U.S. PATENT DOCUMENTS

| 5,268,274 A | 12/1993 | Ben-Bassat et al. ....... 435/69.1 |
| 5,633,439 A | 5/1997 | Walter .................... 800/317.3 |
| 5,646,023 A | 7/1997 | Secor et al. ................ 800/284 |
| 5,654,190 A | 8/1997 | Matsunaga et al. ......... 435/430 |
| 6,013,860 A | 1/2000 | Himmel et al. ............. 800/278 |
| 6,271,443 B1 | 8/2001 | Stalker et al. .............. 800/298 |
| 6,303,847 B1 | 10/2001 | Kawaoka et al. ........... 800/298 |

FOREIGN PATENT DOCUMENTS

| CA | 2012311 | 3/1990 |
| EP | 0 875 575 | 11/1998 |
| WO | WO 98/00549 | 1/1998 |
| WO | WO 98/18949 | 5/1998 |
| WO | WO 00/22092 | 4/2000 |

OTHER PUBLICATIONS

Lazar et al. Molecular and Cellular Biology, vol. 8, No. 3, pp. 1247-1252, 1988.*
Accession No. T10797, pp. 1-2, Sequence Search Result, 1996.*
Bird et al. Biology and Genetic Review, vol. 9, pp. 207-227 (1991).*
Smith et al (Nature, vol. 334, pp. 724-726 (1988).*
Hu, et al., 1999, *Nature Biotechnology*, 17:808-812.
Hu, et al., 1998, *Proc. Natl. Acad. Sci.* 95:5407-5412.
Saxena, et al., 1990, *Plant Molecular Biology*, 15:673-683.
Salvucci, et al., 1993, *Plant Physiol.*, 529-536.
Matton, et al., 1993, *Plant Molecular Biology*, 22:279-291.
Pear, et al., 1996, *Proc. Natl. Acad. Sci.*, 93:12637-12642.
Higuchi, 1997, *Biochemistry and Molecular Biology of Wood*, Springer-Verlag.
Timmel, 1986, *Plant Anatomy*, "Compression Wood in Gymnosperms" Springer-Verlag.
Delmer and Amor, 1995, *Pl. Cell*, 7:987-1000.
Brown, et al., 1996, *Trends Pl. Sci.*, 1:149-156.
Haigler and Blanton, 1996, *PNAS*, 93:12082-12085.
Ye and Varner, 1993.
Fukuda, 1996, *Ann. Rev. Pl. Physiol. Pl. Mol. Biol.*, 47:299-325.
Whetten, et al., 1998, *Ann. Rev. Pl. Physiol. Pl. Mol. Biol.*, 49:585-609.

(Continued)

*Primary Examiner*—Medina A. Ibrahim
(74) *Attorney, Agent, or Firm*—Michael Best & Friedrich LLP

(57) ABSTRACT

The invention relates to isolated polynucleotides encoding functional cellulose synthases and UDP-glucose binding domain thereof, transgenic plants and plant cells transformed with the polynucleotides. The invention further relates to methods of transforming plants and plant cells with cellulose synthase or UDP-encoding polynucleotides.

26 Claims, 10 Drawing Sheets

OTHER PUBLICATIONS

Arioli, et al. 1998, *Science*, 279-717-720.
Wu, et al., 1998, *Pl. Physiol.* 117:1125.
Wu, et al., 1992, *J. Biol. Chem.*, 267:963-967.
Wu and Wu, 1988, *J. Biol. Chem.*, 263:14621-14624.
Needleman and Wunsch, 1970, *J. Mol. Biol.*, 48:443-453.
*Molecular Cloning: A Laboratory Manual*, Sambrook, Fritsch & Maniatis. 1989, 2$^{nd}$ Ed.
*DNA Cloning: A Practical Approach*, 1985. vols. I and II, D.N. Glover ed.
*Oligonucleotide Synthesis*, 1984, M.J. Gait ed.
*Nucleic Acid Hybridization*, 1985, B.D. Hames and J.J. Higgins, eds.
*Transcription And Translation*, 1984, B.D. Hames and J.J. Higgins, eds.
*Animal Cell Culture*, 1986, R.I. Freshney, ed.
Perbal, B., 1984, *A Practical Guide to Molecular Cloning*.
Ausubel, F.M. et al. eds., 1994, *Current Protocols in Molecular Biology*. John Wiley & Sons.
Zoller and Smith, 1984, *DNA*, 3:479-488.
Oliphant, et al., 1986, *Gene*, 44:177.
Hutchinson, et al., 1986, *Proc. Natl. Acad. Sci.*, 83:710.
Higuchi, 1989, *PCR Technology: Principles and Applications for DNA Amplifications for DNA*, H. Erlich, ed., Ch 6, 61-70.
Hoffman and Stoffel, 1993, *Biol. Chem.*, Hoppe-Seyler 374:166.
Benton and Davis, 1977, *Science*, 196:180.
Grunstein and Hogness, 1975, *Proc. Natl. Acad. Sci.*, 72:3961.
Bugos, et al., 1995, *Biotechniques*, 19:734-737.
Alt-Mörbe, et al., 1989, *Mol. Plant-Microbe Interac.* 2:301.
Fullner, et al., 1996, *Science*, 273:1107.
Fullner and Nester, 1996, *J. Bacteriol.*, 178:1498.
Ge and Chiang, 1996, *Pl. Physiol.*, 112:861.
Esau, K., 1960, *Anatomy of Seed Plants*, New York: John Wiley and Sons.
Joshi, et al., 1997, *PMB*, 35:993-1001.
Joshi, et al., 1987, *NAR*, 15:6643-6653.
Joshi, et al., 1987, *NAR*, 15:9627-9640.
Accession No. AF072131 [gi: 4115904], pp. 1-2, Sequence Search Result, Jan. 8, 1999.
Accession No. AF072131 [gi: 3243277], pp. 1, Sequence Search Result, Jun. 23, 1998.
Accession No. AF062485 [gi: 3135610], pp. 1-3, Sequence Search Result, Aug. 8, 1998.
Database EMBL Online, Jun. 23, 1998, Wu. L., Joshi, CP, Chiang, VL, "Populus tremuloides secondary xylem cellulose synthase (cel A) mRNA, complete cds." EBI Database accession No. af072131, Abstract.
Database Swall Online, May 1, 1997, "Cellulose synthase, CELAI", accession No. P93155, Abstract.
Database Swall Online, Nov. 1, 1998, "Secondary xylem cellulose synthase (cel A) mRNA, complete eds." EBI Database accession No. 081368, Abstract.
Nakai, et al., "Control of expression by the cellulose synthase (*bcsA*) promoter region from *Acetobacter xylinum* BPR 2002", *Gene*, 213(1-2):93-100, (1998).
Hutchinson, C., et al., "Mutagenesis at a Specific Position in a DNA Sequence", *J. Biol. Chem.*, 253(18):6551-6560 (1978).
Esau, K., Plant Anatomy, 2$^{nd}$ ed. New York: Wiley (1953).
Esau, K., Anatomy of Seed Plants, New York: Wiley (1960).
Esau, K., Vascular Differentiation in Plants, New York: Holt, Rinehart & Winston (1965).
Esau, K., et al., "Observations on Cytokinesis", *Planta* (Berl.) 67, 168-181 (1965).
Esau, K., "Anatomy of Plant Virus Infections", *Annu. Rev. Phytopathol.* 5:45-76 (1967).
Zhou Y., et al., "Molecular cloning of cellulose synthase genes from loblolly pine", Poster presented at American Society of Plant Biologists annual meeting at Denver, CO, Aug. 2-7, 2002, Abstract 321.
Lu, Shan-Fa, et al., Molecular cloning and characterization of three cellulose synthases associated with xylem development in *Eucalyptus grandis*, Poster presented at American Society of Plant Biologists annual meeting at Denver, CO, Aug. 2-7, 2002, Abstract 320.
Ye and Varner, Plant Physiology 103(3):805-813 (Nov. 1993).
Ye and Varner, Methods in Enzymology 218:671-681 (1993).

\* cited by examiner

Fig. 1: DNA and predicted protein sequence of PtCelA cDNA

```
   1 GTCGACCCACGCGTCCGTCTTGAAAGAATATGAAGTTGTAAAGAGCTGGTAAAGTGGTAA    60
  61 TAAGCAAGATGATGGAATCTGGGGCTCCTATATGCCATACCTGTGGTGAACAGGTGGGGC   120
             M  M  E  S  G  A  P  I  C  H  T  C  G  E  Q  V  G  H
 121 ATGATGCAAATGGGGAGCTATTTGTGGCTTGCCATGAGTGTAGCTATCCATGTGCAAGT   180
      D  A  N  G  E  L  F  V  A  C  H  E  C  S  Y  P  M  C  K  S
 181 CTTGTTTCGAGTTTGAAATCAATGAGGGCCGGAAAGTTTGCTTGCGGTGTGGCTCGCCAT   240
      C  F  E  F  E  I  N  E  G  R  K  V  C  L  R  C  G  S  P  Y
 241 ATGATGAGAACTTGCTGGATGATGTAGAAAAGAAGGGGTCTGGCAATCAATCCACAATGG   300
      D  E  N  L  L  D  D  V  E  K  K  G  S  G  N  Q  S  T  M  A
 301 CATCTCACCTCAACGATTCTCAGGATGTCGGAATCCATGCTAGACATATCAGTAGTGTGT   360
      S  H  L  N  D  S  Q  D  V  G  I  H  A  R  H  I  S  S  V  S
 361 CCACTGTGGATAGTGAAATGAATGATGAATATGGGAATCCAATTTGGAAGAATCGGGTGA   420
      T  V  D  S  E  M  N  D  E  Y  G  N  P  I  W  K  N  R  V  K
 421 AGAGCTGTAAGGATAAAGAGAACAAGAAGAAAAAGAGAAGTCCTAAGGCTGAAACTGAAC   480
      S  C  K  D  K  E  N  K  K  K  K  R  S  P  K  A  E  T  E  P
 481 CAGCTCAAGTTCCTACAGAACAGCAGATGGAAGAGAAACCGTCTGCAGAGGCTTCGGAGC   540
      A  Q  V  P  T  E  Q  Q  M  E  E  K  P  S  A  E  A  S  E  P
 541 CGCTTTCAATTGTTTATCCAATTCCACGCAACAAGCTCACACCATACAGAGCAGTGATCA   600
      L  S  I  V  Y  P  I  P  R  N  K  L  T  P  Y  R  A  V  I  I
 601 TTATGCGACTGGTCATTCTGGGCCTCTTCTTCCACTTCAGAATAACAAATCCTGTCGATA   660
      M  R  L  V  I  L  G  L  F  F  H  F  R  I  T  N  P  V  D  S
 661 GTGCCTTTGGCCTGTGGCTTACTTCTGTCATATGTGAGATCTGGTTTGCATTTTCTTGGG   720
      A  F  G  L  W  L  T  S  V  I  C  E  I  W  F  A  F  S  W  V
 721 TGTTGGATCAGTTCCCCAAGTGGAATCCTGTCAATAGAGAAACGTATATCGAAAGGCTGT   780
      L  D  Q  F  P  K  W  N  P  V  N  R  E  T  Y  I  E  R  L  S
 781 CGGCAAGGTATGAAAGAGAGGGTGAGCCTTCTCAGCTTGCTGGTGTGGATTTTTTCGTGA   840
      A  R  Y  E  R  E  G  E  P  S  Q  L  A  G  V  D  F  F  V  S
 841 GTACTGTTGATCCGCTGAAGGAACCGCCATTGATCACTGCCAATACAGTCCTTTCCATCC   900
      T  V  D  P  L  K  E  P  P  L  I  T  A  N  T  V  L  S  I  L
 901 TTGCTGTGGACTATCCCGTCGATAAAGTCTCCTGCTACGTGTCTGATGATGGTGCAGCTA   960
      A  V  D  Y  P  V  D  K  V  S  C  Y  V  S  D  D  G  A  A  M
 961 TGCTTTCATTTGAATCTCTTGTAGAAACAGCTGAGTTTGCAAGGAAGTGGGTTCCGTTCT  1020
      L  S  F  E  S  L  V  E  T  A  E  F  A  R  K  W  V  P  F  C
1021 GCAAAAAATTCTCAATTGAACCAAGAGCACCGGAGTTTTACTTCTCACAGAAAATTGATT  1080
      K  K  F  S  I  E  P  R  A  P  E  F  Y  F  S  Q  K  I  D  Y
1081 ACTTGAAAGACAAGGTTCAACCTTCTTTCGTGAAAGAACGTAGAGCAATGAAAAGGGATT  1140
      L  K  D  K  V  Q  P  S  F  V  K  E  R  R  A  M  K  R  D  Y
1141 ATGAAGAGTACAAAGTCCGAGTTAATGCCCTGGTAGCAAAGGCTCAGAAAACACCTGAAG  1200
      E  E  Y  K  V  R  V  N  A  L  V  A  K  A  Q  K  T  P  E  E
```

```
1201  AAGGATGGACTATGCAAGATGGAACACCTTGGCCTGGGAATAACACACGTGATCACCCTG  1260
       G  W  T  M  Q  D  G  T  P  W  P  G  N  N  T  R  D  H  P  G
1261  GGCATGATTCAGGTCTTCCTTGGGAAATACTGGGAGCTCGTGACATTGAAGGAAATGAAC  1320
       H  D  S  G  L  P  W  E  I  L  G  A  R  D  I  E  G  N  E  L
1321  TACCTCGTCTAGTATATGTCTCCAGGGAGAAGAGACCTGGCTACCAGCACCACAAAAAGG  1380
       P  R  L  V  Y  V  S  R  E  K  R  P  G  Y  Q  H  H  K  K  A
1381  CTGGTGCAGAAAATGCTCTGGTGAGAGTGTCTGCAGTACTCACAAATGCTCCCTACATCC  1440
       G  A  E  N  A  L  V  R  V  S  A  V  L  T  N  A  P  Y  I  L
1441  TCAATGTTGATTGTGATCACTATGTAAACAATAGCAAGGCTGTTCGAGAGGCAATGTGCA  1500
       N  V  D  C  D  H  Y  V  N  N  S  K  A  V  R  E  A  M  C  I
1501  TCCTGATGGACCCACAAGTAGGTCGAGATGTATGCTATGTGCAGTTCCCTCAGAGGTTTG  1560
       L  M  D  P  Q  V  G  R  D  V  C  Y  V  Q  F  P  Q  R  F  D
1561  ATGGCATAGATAAGAGTGATCGCTACGCCAATCGTAACGTAGTTTTCTTTGATGTTAACA  1620
       G  I  D  K  S  D  R  Y  A  N  R  N  V  V  F  F  D  V  N  M
1621  TGAAAGGGTTGGATGGCATTCAAGGACCAGTATACGTAGGAACTGGTTGTGTTTTCAACA  1680
       K  G  L  D  G  I  Q  G  P  V  Y  V  G  T  G  C  V  F  N  R
1681  GGCAAGCACTTTACGGCTACGGGCCTCCTTCTATGCCCAGCTTACGCAAGAGAAAGGATT  1740
       Q  A  L  Y  G  Y  G  P  P  S  M  P  S  L  R  K  R  K  D  S
1741  CTTCATCCTGCTTCTCATGTTGCTGCCCCTCAAAGAAGAAGCCTGCTCAAGATCCAGCTG  1800
       S  S  C  F  S  C  C  C  P  S  K  K  K  P  A  Q  D  P  A  E
1801  AGGTATACAGAGATGCAAAAAGAGAGGATCTCAATGCTGCCATATTTAATCTTACAGAGA  1860
       V  Y  R  D  A  K  R  E  D  L  N  A  A  I  F  N  L  T  E  I
1861  TTGATAATTATGACGAGCATGAAAGGTCAATGCTGATCTCCCAGTTGAGCTTTGAGAAAA  1920
       D  N  Y  D  E  H  E  R  S  M  L  I  S  Q  L  S  F  E  K  T
1921  CTTTTGGCTTATCTTCTGTCTTCATTGAGTCTACACTAATGGAGAATGGAGGAGTACCCG  1980
       F  G  L  S  S  V  F  I  E  S  T  L  M  E  N  G  G  V  P  E
1981  AGTCTGCCAACTCACCACCATTCATCAAGGAAGCGATTCAAGTCATCGGCTGTGGCTATG  2040
       S  A  N  S  P  P  F  I  K  E  A  I  Q  V  I  G  C  G  Y  E
2041  AAGAGAAGACTGAATGGGGAAAACAGATTGGTTGGATATATGGGTCAGTCACTGAGGATA  2100
       E  K  T  E  W  G  K  Q  I  G  W  I  Y  G  S  V  T  E  D  I
2101  TCTTAAGTGGCTTCAAGATGCACTGCCGAGGATGGAGATCAATTTACTGCATGCCCGTAA  2160
       L  S  G  F  K  M  H  C  R  G  W  R  S  I  Y  C  M  P  V  R
2161  GGCCTGCATTCAAAGGATCTGCACCCATCAACCTGTCTGATAGATTGCACCAGGTCCTCC  2220
       P  A  F  K  G  S  A  P  I  N  L  S  D  R  L  H  Q  V  L  R
2221  GATGGGCTCTTGGTTCTGTGGAAATTTTCTTTAGCAGACACTGTCCCCTCTGGTACGGGT  2280
       W  A  L  G  S  V  E  I  F  F  S  R  H  C  P  L  W  Y  G  F
2281  TTGGAGGAGGCCGTCTTAAATGGCTCCAAAGGCTTGCGTATATAAACACCATTGTGTACC  2340
       G  G  G  R  L  K  W  L  Q  R  L  A  Y  I  N  T  I  V  Y  P
2341  CATTTACATCCCTCCCTCTCATTGCCTATTGCACAATTCCTGCAGTTTGTCTGCTCACCG  2400
       F  T  S  L  P  L  I  A  Y  C  T  I  P  A  V  C  L  L  T  G
2401  GAAAATTCATCATACCAACGCTCTCAAACCTGGCAAGCATGCTGTTTCTTGGCCTCTTTA  2460
       K  F  I  I  P  T  L  S  N  L  A  S  M  L  F  L  G  L  F  I
2461  TCTCCATCATTGTAACTGCGGTGCTTGAGCTAAGATGGAGCGGTGTCAGCATTGAAGATT  2520
```

```
              S   I   I   V   T   A   V   L   E   L   R   W   S   G   V   S   I   E   D   L
2521 TATGGCGTAATGAACAATTCTGGGTGATCGGAGGTGTTTCAGCCCATCTCTTTGCGGTCT 2580
         W   R   N   E   Q   F   W   V   I   G   G   V   S   A   H   L   F   A   V   F
2581 TCCAGGGATTCTTAAAAATGTTGGCTGGCATCGATACGAACTTCACTGTCACAGCAAAAG 2640
         Q   G   F   L   K   M   L   A   G   I   D   T   N   F   T   V   T   A   K   A
2641 CAGCCGAAGATGCAGAATTTGGGGACCTATATATGGTCAAGTGGACAACACTTTTGATTC 2700
         A   E   D   A   E   F   G   E   L   Y   M   V   K   W   T   T   L   L   I   P
2701 CTCCAACCACACTTCTCATTATCAATATGTCGGGTTGTGCTGGATTCTCTGATGCACTCA 2760
         P   T   T   L   L   I   I   N   M   S   G   A   G   F   S   D   A   L   N
2761 ACAAAGGATATGAAGCATGGGGGCCTCTCTTTGGCAAGGTGTTCTTTGCTTTCTGGGTGA 2820
         K   G   Y   E   A   W   G   P   L   F   G   K   V   F   F   A   F   W   V   I
2821 TTCTTCATCTCTATCCATTCCTTAAAGGTCTAATGGGTCGCCAAAACCTAACACCAACCA 2880
         L   H   L   Y   P   F   L   K   G   L   M   G   R   Q   N   L   T   P   T   I
2881 TTGTTGTTCTCTGGTCAGTGCTGTTGGCCTCTGTCTTCTCTCGTTTGGGTCAAGATCA 2940
         V   V   L   W   S   V   L   L   A   S   V   F   S   L   V   W   V   K   I   N
2941 ATCCATTCGTTAACAAAGTTGATAACACCTTGGTTGCGGAGACCTGCATTTCCATTGATT 3000
         P   F   V   N   K   V   D   N   T   L   V   A   E   T   C   I   S   I   D   C
3001 GCTGAGCTACCTCCAATAAGTCTCTCCCAGTATTTTGGGGTTACAAAACCTTTGGGAATT 3060
         *
3061 GGAATATGATCCTCGTTGTAGTTTCCCTCAAGAAAGCACATATCGCTGTCAGTATTTAAA 3120
3121 TGAACTGCAAGATGATTGTTCTCTATGAAGTTTTGAACAGTTTGAAATGATATTATGTTA 3180
3181 AAATACAGGTTTTGATTGTGTTGAAAAAAAAAAAGAAAAAAAAAAAAAAAA 3232
```

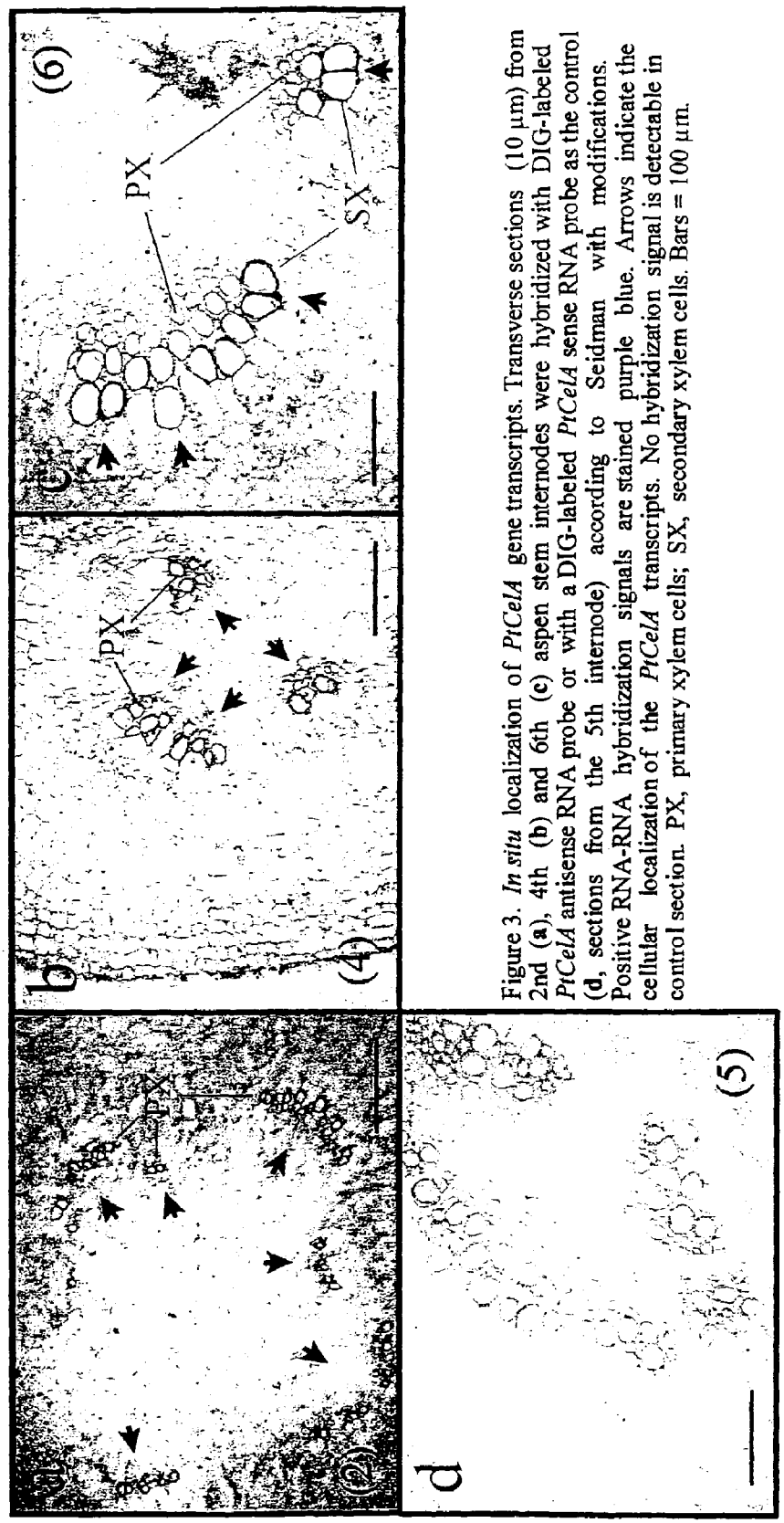

Figure 3. *In situ* localization of *PtCelA* gene transcripts. Transverse sections (10 μm) from 2nd (a), 4th (b) and 6th (c) aspen stem internodes were hybridized with DIG-labeled *PtCelA* antisense RNA probe or with a DIG-labeled *PtCelA* sense RNA probe as the control (d, sections from the 5th internode) according to Seidman with modifications. Positive RNA-RNA hybridization signals are stained purple blue. Arrows indicate the cellular localization of the *PtCelA* transcripts. No hybridization signal is detectable in control section. PX, primary xylem cells; SX, secondary xylem cells. Bars = 100 μm.

FIG. 3

Fig. 4: DNA sequence of PtCelAP, the 5' flanking region of PtCelA coding sequence

```
  1  GAATTCGCCCTTTTGAATTCAGGAGACGATAGTTTCCGGTTCGTTGAATGGCTTTGTTCA   60
 61  CTTCTGGTCTAGCAATTTGCAAAAGAAGTTACAAAACAAATGCATATTATGTAAATTTAA  120
121  CAAGAGATGGGTTCTATGGTCACTTATTTATGCCCATCATTTGTTCTGGGGTTACTCTTT  180
181  ATAGTCTGATTCGAAGTTGCAAACTGCCGTTTCTGGTATTGCAATTATGTAGCCATAAAC  240
241  TGTTAATCCTGTAGCTATTAGCGGACCAACAACCAGATATACGGGATCAGCGTCGTAAAA  300
301  GAGATCTCCATTCTACGTTTCTTTCTAATTTTTCCGTTTCAGTGAGAGAATTACCCTGAT  360
361  ACATTGACATGATGATTGATGATTATGGGAACCATTCCGATGTTAGACACGAGACCATCT  420
421  GGATCCTGCCAGTTTTCAGTTCACATGGCATCTCAGCCCAAGATCATGTGTTTATACGCC  480
481  TAATGACTTGTATTGAAAGTTTGGTAAGTTGAAGATGTGCTCTGCCCAACAGAAACCTTC  540
541  CTTAAATTTCCAGCAAATCTTTCAAACTTGGCCTTACACCCCGAAAATAGACGTGCTTCT  600
601  ACTTGGGTTCTTGGAAACCATGCACCAACCGCCATACCCCACCAACCCACCACCCTCAAC  660
661  CTTCTCTTCGCCATTACAAAAATGTCAGTACCACCCTCTGAAAGACACCAACACACCCTA  720
721  GCTTTGGTTAGGGTATTTGATATAAAAACAAGGCCAAAACAAAAGATTGGAAGGAAGCAG  780
781  AGGAAGACCCTCTTGAAAGAATTGAAGTTGTAAAGAGCTGGTAAAGTGGTAATAAGCAAG  840
841  ATGATGGAATCTGGGGCTCCTATATGCCATACCTGTGGTGAACAGGTGGGGCATGATGCA  900
      M   M   E   S   G   A   P   I   C   H   T   C   G   E   Q   V   G   H   D   A
901  AATGGGGAGCTATTTGTGGCTTGCCATGAGTGTAGCTATCCCATGTGCAAGTCTTGTTTC  960
      N   G   E   L   F   V   A   C   H   E   C   S   Y   P   M   C   K   S   C   F
961  GAGTTTGAAATCAAAGAGGGCCGGAAAGTTTGCTTGCGGTGTGGCTCGAG           1010
      E   F   E   I   K   E   G   R   K   V   C   L   R   C   G   S
```

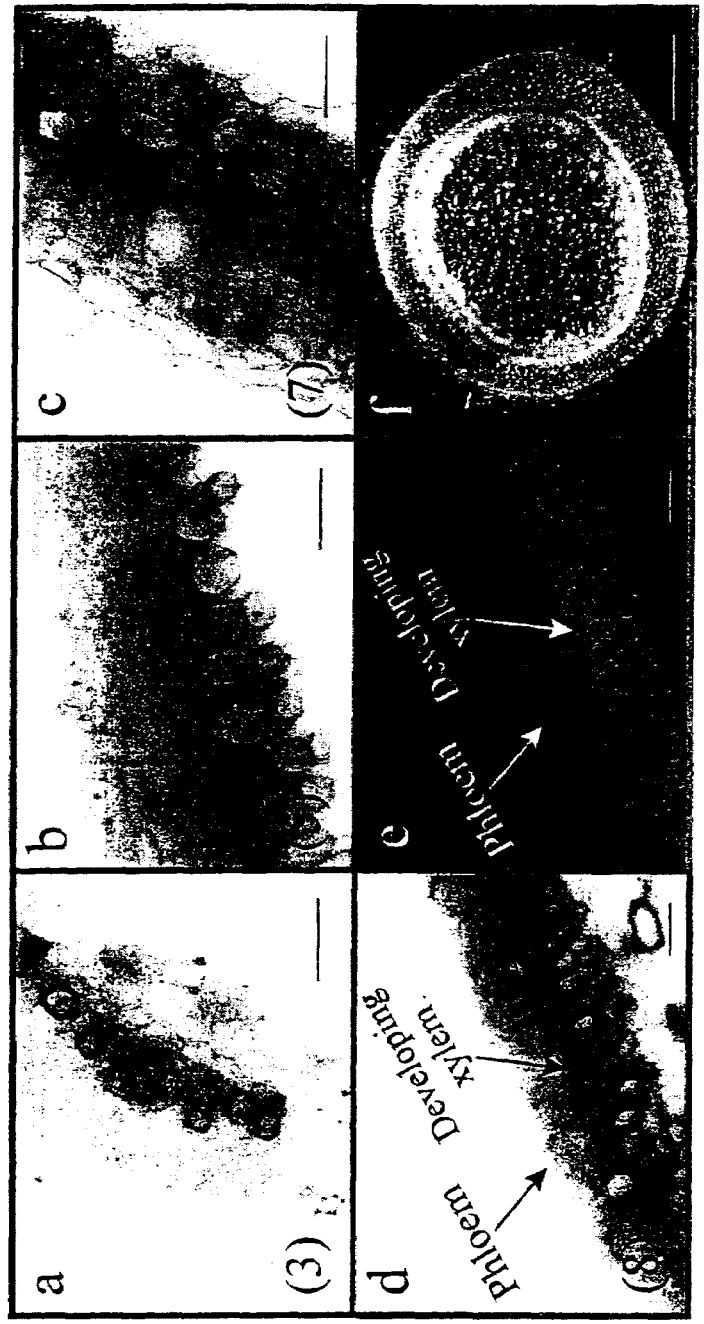

Figure 5. Histochemical analysis of transgenic tobacco for GUS gene expression driven by aspen PtCelA gene promoter. Stem transverse sections from the 3rd (a), 5th (b), 7th (c), and 8th (d and f) internodes were stained for GUS activity. Fluorescence microscopy (e) showing the identical section as in (d). Lignin autofluorescence was visualized after UV irradiation. An entire section from the 8th internode stained for GUS activity is shown in (f). Bars = 100 μm in a to e; bar = 1.5 mm in f.

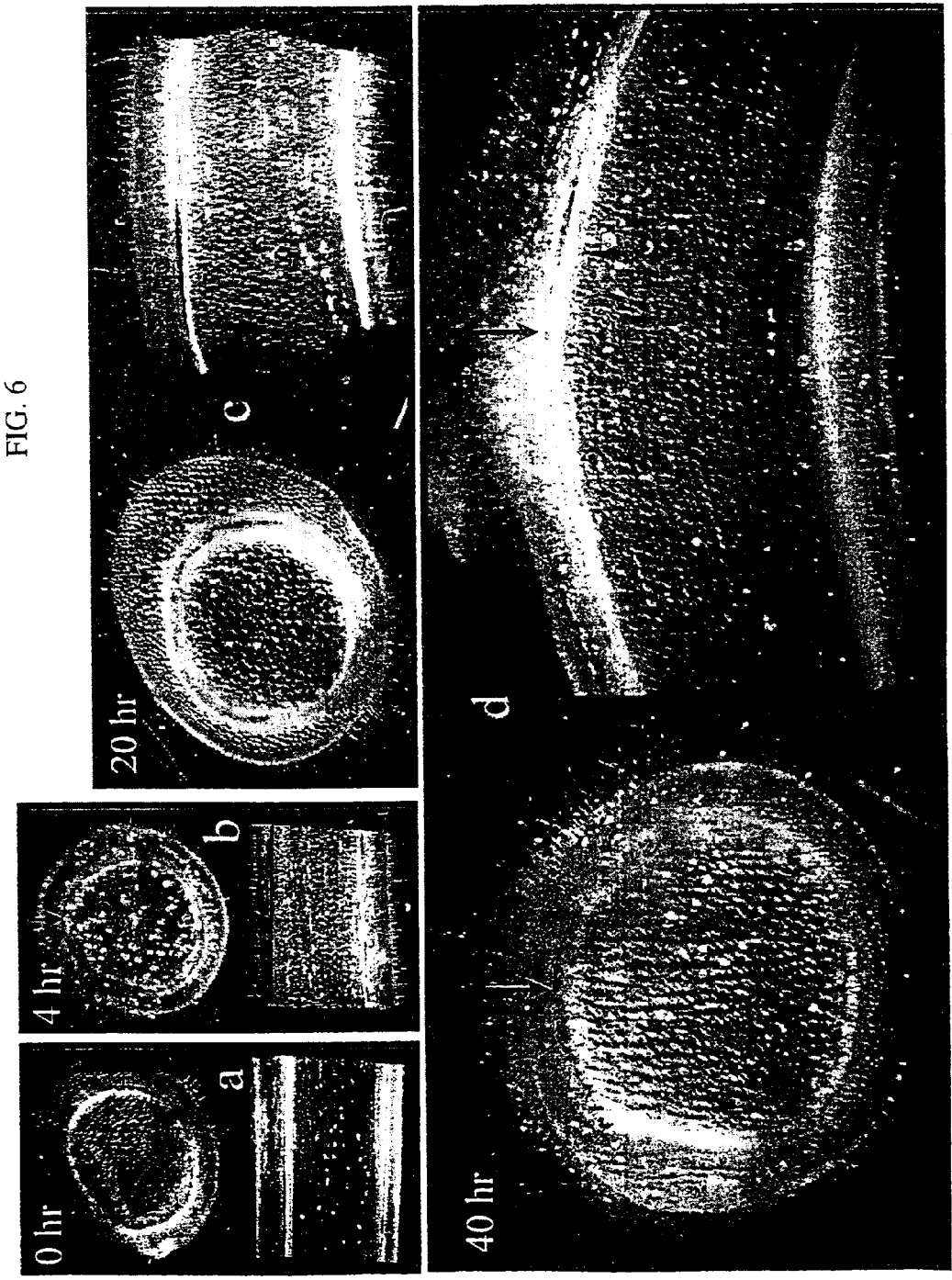
Figure 6. GUS gene expression driven by aspen PtCelA gene promoter in transgenic tobacco plants under tension stress. Tension stress was induced by bending the transgenic plants. Tangential and longitudinal sections were harvested before bending (a) and 4 (b), 20 (c) and 40 (d) hours after bending and stained for GUS expression. Arrows indicate the bend sites.

FIG. 7

Arabidopsis thaliana cellulose synthase mRNA SEQ ID NO: 4

```
   1 gcggccgcgg ttaatcgccg gttctcacaa caggaatgag tttgtcctca ttaatgccga
  61 tgagaatgcc cgaataagat cagtccaaga gctgagtgga cagacatgtc aaatctgcag
 121 agatgagatc gaattgactg ttgatggaga accgtttgtg gcatgtaacg aatgtgcatt
 181 ccctgtgtgt agaccttgct atgagtacga aagacgagaa ggcaatcaag cttgtccaca
 241 gtgcaaaacc cgtttcaaac gtcttaaagg aagtccaaga gttgaaggtg atgaagagga
 301 agatgacatt gatgatttag acaatgagtt tgagtatgga aataatggga ttggatttga
 361 tcaggttttct gaaggtatgt caatctctcg tcgcaactcc ggtttccac aatctgattt
 421 ggattcagct ccacctggct ctcagattcc attgctgact tacggcgacg aggacgttga
 481 gatttcttct gatagacatg ctcttattgt tcctccttca cttggtggtc atggcaatag
 541 agttcatcct gtttctcttt ctgacccgac cgtggctgca catcgaaggc tgatggtacc
 601 tcagaaagat cttgcggttt atggttatgg aagtgtcgct tggaaagatc ggatggagga
 661 atggaagaga aagcagaatg agaaacttca ggttgttagg catgaaggag atcctgattt
 721 tgaagatggt gatgatgctg attttccaat gatggatgag ggaaggcagc cattgtctat
 781 gaagatacca atcaaatcga gcaagataaa tccttaccgg atgttaattg tgctacgtct
 841 tgtgattctt ggtctcttct ttcactaccg tattcttcac cccgtcaaag atgcatatgc
 901 tttgtggctt atttctgtta tatgtgagat atggtttgct gtttcatggg ttcttgatca
 961 gttccctaaa tggtaccta tcgagcgaga aacgtacttg gaccgactct cattaagata
1021 tgagaaagaa gggaaaccgt cgggactatc ccctgttggat gtatttgtta gtacagtgga
1081 tccattgaaa gagcctccgc ttattactgc aaatactgtc ttgtctattc ttgctgttga
1141 ttatcctgtc gataaggttg cttgttacgt atctgatgat ggtgctgcta tgcttacttt
1201 cgaagctctt tctgagaccg ctgaattcgc aaggaaatgg gttcctttct gcaagaaata
1261 ttgtattgag cctcgtgctc ccgaatggta tttctgccat aaaatggact acttgaagaa
1321 taaagttcat cccgcatttg ttagggagcg gcgagccatg aagagagatt atgaagaatt
1381 caaagtaaag atcaatgctt tagtagcaac agcacagaaa gtgcctgagg atggttggac
1441 tatgcaagac ggtacacctt ggcccggtaa tagtgtgcga gatcatcctg gcatgattca
1501 ggtcttcctt cgaagtgacg gtgttcgtga tgtcgaaaac aacgagttgc ctcgattagt
1561 ttacgtttct cgtgagaaga gacccggatt tgatcaccat aagaaggctg gagctatgaa
1621 ttccctgata cgagtctctg gggttctatc aaatgctcct taccttctga atgtcgattg
1681 tgatcactac atcaacaata gcaaagctct tagagaagca atgtgtttca tgatggatcc
1741 tcagtcagga aagaaaatct gttatgttca gttccctcaa aggttcgatg ggattgatag
1801 gcacgatcga tactcaaatc gcaatgttgt gttctttgat atcaatatga aaggtttgga
1861 tgggctacaa gggcctatat acgtcggtac aggttgtgtt ttcaggaggc aagcgcttta
1921 cggatttgat gcaccgaaga agaagaaggg cccacgtaag acatgcaatt gctggccaaa
1981 atggtgtctc ctatgttttg gttcaagaaa gaatcgtaaa gcaaagacag tggctgcgga
2041 taagaagaag aagaataggg aagcgtcaaa gcagatccac gcattagaaa atatcgaaga
2101 gggccgcggt cataaagttc ttaacgtaga acagtcaacc gaggcaatgc aaatgaagtt
2161 gcagaagaaa tatgggcagt ctcctgtatt tgttgcatct gcgcgtctgg agaatggtgg
2221 gatggctaga aacgcaagcc cggcttgtct gcttaaagaa gccatccaag tcattagtcg
2281 cggatatgaa gataaaactg aatggggaaa agagattggg tggatctatg gttctgttac
2341 cgaagatatt cttacgggtt ctaagatgca ttctcatggt tggagacatg tttattgtac
2401 accaaagtta gcggctttca aaggatcagc tccaatcaat ctttcggatc gtctccatca
2461 agttcttcga tgggcgcttg ggtcggttga gattttcttg agtaggcatt gtcctatttg
2521 gtatggttat ggaggtgggt tgaaatggct tgagcggttg tcctacatta actctgtggt
2581 ttaccgtgg acctctctac cgctcatcgt ttactgttct ctccctgcca tctgtcttct
2641 cactggaaaa ttcatcgtc ccgagattag caactatgcg agtatcctct tcatggcgct
2701 cttctcgtcg attgcaataa cgggtattct cgagatgcaa tggggcaaag ttgggatcga
2761 tgattggtgg agaaacgaac agttttgggt cattggaggt gtttctgcgc atctgtttgc
2821 tctcttccaa ggtctcctca aggttcttgc tggtgtcgac actaacttca cagtcacatc
2881 aaaagcagct gatgatggag agttctctga cctttacctc ttcaaatgga cttcacttct
2941 catccctcca atgactctac tcatcataaa cgtcattgga gtcatagtcg gagtctctga
3001 tgccatcagc aatggatacg actcgtgggg accgctttc ggaagactgt tctttgcact
3061 ttgggtcatc attcatcttt acccgttcct taaaggtttg cttgggaaac aagatagaat
3121 gccaaccatt attgtcgtct ggtccatcct cctggcctcg attcttacac ttctttgggt
3181 ccgggttaat ccgtttgtgg cgaaaggcgg tcctattctc gagatctgtg tttagactg
3241 cttgtgattc gattgaccgg tggatgggtt ggtgaaaaag gtttaattcc cacggatcaa
3301 agagaggtaa gagagatatt gttttacctc taaaagactc cttcattgtg ttcattagat
3361 gatgaaaaat gaaaagaaaa agaagattta attttgttac gagaattgtt attttgcaa
3421 gaatgtgttg tagatagcgg ccgc
```

FIG. 8

Arabidopsis thaliana cellulose synthase SEQ ID NO: 5

RPRLIAGSHNRNEFVLINADENARIRSVQELSGQTCQICRDEIE

LTVDGEPFVACNECAFPVCRPCYEYERREGNQACPQCKTRFKRLKGSPRVEGDEEEDD

IDDLDNEFEYGNNGIGFDQVSEGMSISRRNSGFPQSDLDSAPPGSQIPLLTYGDEDVE

ISSDRHALIVPPSLGGHGNRVHPVSLSDPTVAAHRRLMVPQKDLAVYGYGSVAWKDRM

EEWKRKQNEKLQVVRHEGDPDFEDGDDADFPMMDEGRQPLSMKIPIKSSKINPYRMLI

VLRLVILGLFFHYRILHPVKDAYALWLISVICEIWFAVSWVLDQFPKWYPIERETYLD

RLSLRYEKEGKPSGLSPVDVFVSTVDPLKEPPLITANTVLSILAVDYPVDKVACYVSD

DGAAMLTFEALSETAEFARKWVPFCKKYCIEPRAPEWYFCHKMDYLKNKVHPAFVRER

RAMKRDYEEFKVKINALVATAQKVPEDGWTMQDGTPWPGNSVRDHPGMIQVFLGSDGV

RDVENNELPRLVYVSREKRPGFDHHKKAGAMNSLIRVSGVLSNAPYLLNVDCDHYINN

SKALREAMCFMMDPQSGKKICYVQFPQRFDGIDRHDRYSNRNVVFFDINMKGLDGLQG

PIYVGTGCVFRRQALYGFDAPKKKKGPRKTCNCWPKWCLLCFGSRKNRKAKTVAADKK

KKNREASKQIHALENIEEGRGHKVLNVEQSTEAMQMKLQKKYGQSPVFVASARLENGG

MARNASPACLLKEAIQVISRGYEDKTEWGKEIGWIYGSVTEDILTGSKMHSHGWRHVY

CTPKLAAFKGSAPINLSDRLHQVLRWALGSVEIFLSRHCPIWYGYGGGLKWLERLSYI

NSVVYPWTSLPLIVYCSLPAICLLTGKFIVPEISNYASILFMALFSSIAITGILEMQW

GKVGIDDWWRNEQFWVIGGVSAHLFALFQGLLKVLAGVDTNFTVTSKAADDGEFSDLY

LFKWTSLLIPPMTLLIINVIGVIVGVSDAISNGYDSWGPLFGRLFFALWVIIHLYPFL

KGLLGKQDRMPTIIVVWSILLASILTLLWVRVNPFVAKGGPILEICGLDCL

SEQUENCE LISTING

```
<160> NUMBER OF SEQ ID NOS: 7

<210> SEQ ID NO 1
<211> LENGTH: 3232
<212> TYPE: DNA
<213> ORGANISM: Populus tremuloides
<220> FEATURE:
<221> NAME/KEY: CDS
<222> LOCATION: (69)..(3002)

<400> SEQUENCE: 1
gtcgacccac gcgtccgtct tgaaagaata tgaagttgta aagagctggt aaagtggtaa      60 taagcaag atg atg gaa tct ggg gct cct ata tgc cat acc tgt ggt gaa     110
         Met Met Glu Ser Gly Ala Pro Ile Cys His Thr Cys Gly Glu
           1               5                  10 cag gtg ggg cat gat gca aat ggg gag cta ttt gtg gct tgc cat gag     158
Gln Val Gly His Asp Ala Asn Gly Glu Leu Phe Val Ala Cys His Glu
 15                  20                  25                  30 tgt agc tat ccc atg tgc aag tct tgt ttc gag ttt gaa atc aat gag     206
Cys Ser Tyr Pro Met Cys Lys Ser Cys Phe Glu Phe Glu Ile Asn Glu
                 35                  40                  45 ggc cgg aaa gtt tgc ttg cgg tgt ggc tcg cca tat gat gag aac ttg     254
Gly Arg Lys Val Cys Leu Arg Cys Gly Ser Pro Tyr Asp Glu Asn Leu
             50                  55                  60 ctg gat gat gta gaa aag aag ggg tct ggc aat caa tcc aca atg gca     302
Leu Asp Asp Val Glu Lys Lys Gly Ser Gly Asn Gln Ser Thr Met Ala
         65                  70                  75
```

```
tct cac ctc aac gat tct cag gat gtc gga atc cat gct aga cat atc      350
Ser His Leu Asn Asp Ser Gln Asp Val Gly Ile His Ala Arg His Ile
    80              85                  90 agt agt gtg tcc act gtg gat agt gaa atg aat gat gaa tat ggg aat      398
Ser Ser Val Ser Thr Val Asp Ser Glu Met Asn Asp Glu Tyr Gly Asn
 95             100                 105                 110 cca att tgg aag aat cgg gtg aag agc tgt aag gat aaa gag aac aag      446
Pro Ile Trp Lys Asn Arg Val Lys Ser Cys Lys Asp Lys Glu Asn Lys
                115                 120                 125 aag aaa aag aga agt cct aag gct gaa act gaa cca gct caa gtt cct      494
Lys Lys Lys Arg Ser Pro Lys Ala Glu Thr Glu Pro Ala Gln Val Pro
            130                 135                 140 aca gaa cag cag atg gaa gag aaa ccg tct gca gag gct tcg gag ccg      542
Thr Glu Gln Gln Met Glu Glu Lys Pro Ser Ala Glu Ala Ser Glu Pro
        145                 150                 155 ctt tca att gtt tat cca att cca cgc aac aag ctc aca cca tac aga      590
Leu Ser Ile Val Tyr Pro Ile Pro Arg Asn Lys Leu Thr Pro Tyr Arg
160                 165                 170 gca gtg atc att atg cga ctg gtc att ctg ggc ctc ttc ttc cac ttc      638
Ala Val Ile Ile Met Arg Leu Val Ile Leu Gly Leu Phe Phe His Phe
175                 180                 185                 190 aga ata aca aat cct gtc gat agt gcc ttt ggc ctg tgg ctt act tct      686
Arg Ile Thr Asn Pro Val Asp Ser Ala Phe Gly Leu Trp Leu Thr Ser
                195                 200                 205 gtc ata tgt gag atc tgg ttt gca ttt tct tgg gtg ttg gat cag ttc      734
Val Ile Cys Glu Ile Trp Phe Ala Phe Ser Trp Val Leu Asp Gln Phe
            210                 215                 220 ccc aag tgg aat cct gtc aat aga gaa acg tat atc gaa agg ctg tcg      782
Pro Lys Trp Asn Pro Val Asn Arg Glu Thr Tyr Ile Glu Arg Leu Ser
        225                 230                 235 gca agg tat gaa aga gag ggt gag cct tct cag ctt gct ggt gtg gat      830
Ala Arg Tyr Glu Arg Glu Gly Glu Pro Ser Gln Leu Ala Gly Val Asp
    240                 245                 250 ttt ttc gtg agt act gtt gat ccg ctg aag gaa ccg cca ttg atc act      878
Phe Phe Val Ser Thr Val Asp Pro Leu Lys Glu Pro Pro Leu Ile Thr
255                 260                 265                 270 gcc aat aca gtc ctt tcc atc ctt gct gtg gac tat ccc gtc gat aaa      926
Ala Asn Thr Val Leu Ser Ile Leu Ala Val Asp Tyr Pro Val Asp Lys
                275                 280                 285 gtc tcc tgc tac gtg tct gat gat ggt gca gct atg ctt tca ttt gaa      974
Val Ser Cys Tyr Val Ser Asp Asp Gly Ala Ala Met Leu Ser Phe Glu
            290                 295                 300 tct ctt gta gaa aca gct gag ttt gca agg aag tgg gtt ccg ttc tgc     1022
Ser Leu Val Glu Thr Ala Glu Phe Ala Arg Lys Trp Val Pro Phe Cys
        305                 310                 315 aaa aaa ttc tca att gaa cca aga gca ccg gag ttt tac ttc tca cag     1070
Lys Lys Phe Ser Ile Glu Pro Arg Ala Pro Glu Phe Tyr Phe Ser Gln
    320                 325                 330 aaa att gat tac ttg aaa gac aag gtt caa cct tct ttc gtg aaa gaa     1118
Lys Ile Asp Tyr Leu Lys Asp Lys Val Gln Pro Ser Phe Val Lys Glu
335                 340                 345                 350 cgt aga gca atg aaa agg gat tat gaa gag tac aaa gtc cga gtt aat     1166
Arg Arg Ala Met Lys Arg Asp Tyr Glu Glu Tyr Lys Val Arg Val Asn
                355                 360                 365 gcc ctg gta gca aag gct cag aaa aca cct gaa gaa gga tgg act atg     1214
Ala Leu Val Ala Lys Ala Gln Lys Thr Pro Glu Glu Gly Trp Thr Met
            370                 375                 380 caa gat gga aca cct tgg cct ggg aat aac aca cgt gat cac cct ggg     1262
Gln Asp Gly Thr Pro Trp Pro Gly Asn Asn Thr Arg Asp His Pro Gly
        385                 390                 395
```

```
cat gat tca ggt ctt cct tgg gaa ata ctg gga gct cgt gac att gaa    1310
His Asp Ser Gly Leu Pro Trp Glu Ile Leu Gly Ala Arg Asp Ile Glu
    400                 405                 410 gga aat gaa cta cct cgt cta gta tat gtc tcc agg gag aag aga cct    1358
Gly Asn Glu Leu Pro Arg Leu Val Tyr Val Ser Arg Glu Lys Arg Pro
415                 420                 425                 430 ggc tac cag cac cac aaa aag gct ggt gca gaa aat gct ctg gtg aga    1406
Gly Tyr Gln His His Lys Lys Ala Gly Ala Glu Asn Ala Leu Val Arg
                435                 440                 445 gtg tct gca gta ctc aca aat gct ccc tac atc ctc aat gtt gat tgt    1454
Val Ser Ala Val Leu Thr Asn Ala Pro Tyr Ile Leu Asn Val Asp Cys
            450                 455                 460 gat cac tat gta aac aat agc aag gct gtt cga gag gca atg tgc atc    1502
Asp His Tyr Val Asn Asn Ser Lys Ala Val Arg Glu Ala Met Cys Ile
        465                 470                 475 ctg atg gac cca caa gta ggt cga gat gta tgc tat gtg cag ttc cct    1550
Leu Met Asp Pro Gln Val Gly Arg Asp Val Cys Tyr Val Gln Phe Pro
    480                 485                 490 cag agg ttt gat ggc ata gat aag agt gat cgc tac gcc aat cgt aac    1598
Gln Arg Phe Asp Gly Ile Asp Lys Ser Asp Arg Tyr Ala Asn Arg Asn
495                 500                 505                 510 gta gtt ttc ttt gat gtt aac atg aaa ggg ttg gat ggc att caa gga    1646
Val Val Phe Phe Asp Val Asn Met Lys Gly Leu Asp Gly Ile Gln Gly
                515                 520                 525 cca gta tac gta gga act ggt tgt gtt ttc aac agg caa gca ctt tac    1694
Pro Val Tyr Val Gly Thr Gly Cys Val Phe Asn Arg Gln Ala Leu Tyr
            530                 535                 540 ggc tac ggg cct cct tct atg ccc agc tta cgc aag aga aag gat tct    1742
Gly Tyr Gly Pro Pro Ser Met Pro Ser Leu Arg Lys Arg Lys Asp Ser
        545                 550                 555 tca tcc tgc ttc tca tgt tgc tgc ccc tca aag aag aag cct gct caa    1790
Ser Ser Cys Phe Ser Cys Cys Cys Pro Ser Lys Lys Lys Pro Ala Gln
    560                 565                 570 gat cca gct gag gta tac aga gat gca aaa aga gag gat ctc aat gct    1838
Asp Pro Ala Glu Val Tyr Arg Asp Ala Lys Arg Glu Asp Leu Asn Ala
575                 580                 585                 590 gcc ata ttt aat ctt aca gag att gat aat tat gac gag cat gaa agg    1886
Ala Ile Phe Asn Leu Thr Glu Ile Asp Asn Tyr Asp Glu His Glu Arg
                595                 600                 605 tca atg ctg atc tcc cag ttg agc ttt gag aaa act ttt ggc tta tct    1934
Ser Met Leu Ile Ser Gln Leu Ser Phe Glu Lys Thr Phe Gly Leu Ser
            610                 615                 620 tct gtc ttc att gag tct aca cta atg gag aat gga gta ccc gag        1982
Ser Val Phe Ile Glu Ser Thr Leu Met Glu Asn Gly Val Pro Glu
        625                 630                 635 tct gcc aac tca cca cca ttc atc aag gaa gcg att caa gtc atc ggc    2030
Ser Ala Asn Ser Pro Pro Phe Ile Lys Glu Ala Ile Gln Val Ile Gly
    640                 645                 650 tgt ggc tat gaa gag aag act gaa tgg gga aaa cag att ggt tgg ata    2078
Cys Gly Tyr Glu Glu Lys Thr Glu Trp Gly Lys Gln Ile Gly Trp Ile
655                 660                 665                 670 tat ggg tca gtc act gag gat atc tta agt ggc ttc aag atg cac tgc    2126
Tyr Gly Ser Val Thr Glu Asp Ile Leu Ser Gly Phe Lys Met His Cys
                675                 680                 685 cga gga tgg aga tca att tac tgc atg ccc gta agg cct gca ttc aaa    2174
Arg Gly Trp Arg Ser Ile Tyr Cys Met Pro Val Arg Pro Ala Phe Lys
            690                 695                 700 gga tct gca ccc atc aac ctg tct gat aga ttg cac cag gtc ctc cga    2222
Gly Ser Ala Pro Ile Asn Leu Ser Asp Arg Leu His Gln Val Leu Arg
```

```
                705                 710                 715
tgg gct ctt ggt tct gtg gaa att ttc ttt agc aga cac tgt ccc ctc      2270
Trp Ala Leu Gly Ser Val Glu Ile Phe Phe Ser Arg His Cys Pro Leu
    720                 725                 730 tgg tac ggg ttt gga gga ggc cgt ctt aaa tgg ctc caa agg ctt gcg      2318
Trp Tyr Gly Phe Gly Gly Gly Arg Leu Lys Trp Leu Gln Arg Leu Ala
735                 740                 745                 750 tat ata aac acc att gtg tac cca ttt aca tcc ctc cct ctc att gcc      2366
Tyr Ile Asn Thr Ile Val Tyr Pro Phe Thr Ser Leu Pro Leu Ile Ala
                755                 760                 765 tat tgc aca att cct gca gtt tgt ctg ctc acc gga aaa ttc atc ata      2414
Tyr Cys Thr Ile Pro Ala Val Cys Leu Leu Thr Gly Lys Phe Ile Ile
            770                 775                 780 cca acg ctc tca aac ctg gca agc atg ctg ttt ctt ggc ctc ttt atc      2462
Pro Thr Leu Ser Asn Leu Ala Ser Met Leu Phe Leu Gly Leu Phe Ile
        785                 790                 795 tcc atc att gta act gcg gtg ctt gag cta aga tgg agc ggt gtc agc      2510
Ser Ile Ile Val Thr Ala Val Leu Glu Leu Arg Trp Ser Gly Val Ser
    800                 805                 810 att gaa gat tta tgg cgt aat gaa caa ttc tgg gtg atc gga ggt gtt      2558
Ile Glu Asp Leu Trp Arg Asn Glu Gln Phe Trp Val Ile Gly Gly Val
815                 820                 825                 830 tca gcc cat ctc ttt gcg gtc ttc cag gga ttc tta aaa atg ttg gct      2606
Ser Ala His Leu Phe Ala Val Phe Gln Gly Phe Leu Lys Met Leu Ala
                835                 840                 845 ggc atc gat acg aac ttc act gtc aca gca aaa gca gcc gaa gat gca      2654
Gly Ile Asp Thr Asn Phe Thr Val Thr Ala Lys Ala Ala Glu Asp Ala
            850                 855                 860 gaa ttt ggg gag cta tat atg gtc aag tgg aca aca ctt ttg att cct      2702
Glu Phe Gly Glu Leu Tyr Met Val Lys Trp Thr Thr Leu Leu Ile Pro
        865                 870                 875 cca acc aca ctt ctc att atc aat atg tcg ggt tgt gct gga ttc tct      2750
Pro Thr Thr Leu Leu Ile Ile Asn Met Ser Gly Cys Ala Gly Phe Ser
    880                 885                 890 gat gca ctc aac aaa gga tat gaa gca tgg ggg cct ctc ttt ggc aag      2798
Asp Ala Leu Asn Lys Gly Tyr Glu Ala Trp Gly Pro Leu Phe Gly Lys
895                 900                 905                 910 gtg ttc ttt gct ttc tgg gtg att ctt cat ctc tat cca ttc ctt aaa      2846
Val Phe Phe Ala Phe Trp Val Ile Leu His Leu Tyr Pro Phe Leu Lys
                915                 920                 925 ggt cta atg ggt cgc caa aac cta aca cca acc att gtt gtt ctc tgg      2894
Gly Leu Met Gly Arg Gln Asn Leu Thr Pro Thr Ile Val Val Leu Trp
            930                 935                 940 tca gtg ctg ttg gcc tct gtc ttc tct ctc gtt tgg gtc aag atc aat      2942
Ser Val Leu Leu Ala Ser Val Phe Ser Leu Val Trp Val Lys Ile Asn
        945                 950                 955 cca ttc gtt aac aaa gtt gat aac acc ttg gtt gcg gag acc tgc att      2990
Pro Phe Val Asn Lys Val Asp Asn Thr Leu Val Ala Glu Thr Cys Ile
    960                 965                 970 tcc att gat tgc tgagctacct ccaataagtc tctcccagta ttttggggtt         3042
Ser Ile Asp Cys
975 acaaaacctt tgggaattgg aatatgatcc tcgttgtagt ttccctcaag aaagcacata    3102 tcgctgtcag tatttaaatg aactgcaaga tgattgttct ctatgaagtt ttgaacagtt    3162 tgaaatgata ttatgttaaa atacaggttt tgattgtgtt gaaaaaaaaa aagaaaaaaa    3222 aaaaaaaaaa                                                           3232
```

```
<210> SEQ ID NO 2
<211> LENGTH: 978
<212> TYPE: PRT
<213> ORGANISM: Populus tremuloides

<400> SEQUENCE: 2
```

| | | | | | | | | | | | | | | |
|---|---|---|---|---|---|---|---|---|---|---|---|---|---|---|
|Met|Met|Glu|Ser|Gly|Ala|Pro|Ile|Cys|His|Thr|Cys|Gly|Glu|Gln|Val|
|1| | | |5| | | |10| | | | |15| |
|Gly|His|Asp|Ala|Asn|Gly|Glu|Leu|Phe|Val|Ala|Cys|His|Glu|Cys|Ser|
| | | |20| | | | |25| | | | |30| | |
|Tyr|Pro|Met|Cys|Lys|Ser|Cys|Phe|Glu|Phe|Glu|Ile|Asn|Gly|Gly|Arg|
| | | | |35| | | | |40| | | | |45| |
|Lys|Val|Cys|Leu|Arg|Cys|Gly|Ser|Pro|Tyr|Asp|Glu|Asn|Leu|Leu|Asp|
| | |50| | | | |55| | | | |60| | | |
|Asp|Val|Glu|Lys|Lys|Gly|Ser|Gly|Asn|Gln|Ser|Thr|Met|Ala|Ser|His|
|65| | | | |70| | | | |75| | | | |80|
|Leu|Asn|Asp|Ser|Gln|Asp|Val|Gly|Ile|His|Ala|Arg|His|Ile|Ser|Ser|
| | | | |85| | | | |90| | | | |95| |
|Val|Ser|Thr|Val|Asp|Ser|Glu|Met|Asn|Asp|Glu|Tyr|Gly|Asn|Pro|Ile|
| | | |100| | | | |105| | | | |110| | |
|Trp|Lys|Asn|Arg|Val|Lys|Ser|Cys|Lys|Asp|Lys|Glu|Asn|Lys|Lys|Lys|
| | | |115| | | | |120| | | | |125| | |
|Lys|Arg|Ser|Pro|Lys|Ala|Glu|Thr|Glu|Pro|Ala|Gln|Val|Pro|Thr|Glu|
| | |130| | | | |135| | | | |140| | | |
|Gln|Gln|Met|Glu|Glu|Lys|Pro|Ser|Ala|Glu|Ala|Ser|Glu|Pro|Leu|Ser|
|145| | | | |150| | | | |155| | | | |160|
|Ile|Val|Tyr|Pro|Ile|Pro|Arg|Asn|Lys|Leu|Thr|Pro|Tyr|Arg|Ala|Val|
| | | | |165| | | | |170| | | | |175| |
|Ile|Ile|Met|Arg|Leu|Val|Ile|Leu|Gly|Leu|Phe|Phe|His|Phe|Arg|Ile|
| | | |180| | | | |185| | | | |190| | |
|Thr|Asn|Pro|Val|Asp|Ser|Ala|Phe|Gly|Leu|Trp|Leu|Thr|Ser|Val|Ile|
| | | |195| | | | |200| | | | |205| | |
|Cys|Glu|Ile|Trp|Phe|Ala|Phe|Ser|Trp|Val|Leu|Asp|Gln|Phe|Pro|Lys|
| | |210| | | | |215| | | | |220| | | |
|Trp|Asn|Pro|Val|Asn|Arg|Glu|Thr|Tyr|Ile|Glu|Arg|Leu|Ser|Ala|Arg|
|225| | | | |230| | | | |235| | | | |240|
|Tyr|Glu|Arg|Glu|Gly|Glu|Pro|Ser|Gln|Leu|Ala|Gly|Val|Asp|Phe|Phe|
| | | | |245| | | | |250| | | | |255| |
|Val|Ser|Thr|Val|Asp|Pro|Leu|Lys|Glu|Pro|Pro|Leu|Ile|Thr|Ala|Asn|
| | | |260| | | | |265| | | | |270| | |
|Thr|Val|Leu|Ser|Ile|Leu|Ala|Val|Asp|Tyr|Pro|Val|Asp|Lys|Val|Ser|
| | | |275| | | | |280| | | | |285| | |
|Cys|Tyr|Val|Ser|Asp|Asp|Gly|Ala|Ala|Met|Leu|Ser|Phe|Glu|Ser|Leu|
| | |290| | | | |295| | | | |300| | | |
|Val|Glu|Thr|Ala|Glu|Phe|Ala|Arg|Lys|Trp|Val|Pro|Phe|Cys|Lys|Lys|
|305| | | | |310| | | | |315| | | | |320|
|Phe|Ser|Ile|Glu|Pro|Arg|Ala|Pro|Glu|Phe|Tyr|Phe|Ser|Gln|Lys|Ile|
| | | | |325| | | | |330| | | | |335| |
|Asp|Tyr|Leu|Lys|Asp|Lys|Val|Gln|Pro|Ser|Phe|Val|Lys|Glu|Arg|Arg|
| | | |340| | | | |345| | | | |350| | |
|Ala|Met|Lys|Arg|Asp|Tyr|Glu|Glu|Tyr|Lys|Val|Arg|Val|Asn|Ala|Leu|
| | | |355| | | | |360| | | | |365| | |
|Val|Ala|Lys|Ala|Gln|Lys|Thr|Pro|Glu|Glu|Gly|Trp|Thr|Met|Gln|Asp|
| | |370| | | | |375| | | | |380| | | |

-continued

```
Gly Thr Pro Trp Pro Gly Asn Asn Thr Arg Asp His Pro Gly His Asp
385                 390                 395                 400

Ser Gly Leu Pro Trp Glu Ile Leu Gly Ala Arg Asp Ile Glu Gly Asn
            405                 410                 415

Glu Leu Pro Arg Leu Val Tyr Val Ser Arg Glu Lys Arg Pro Gly Tyr
            420                 425                 430

Gln His His Lys Lys Ala Gly Ala Glu Asn Ala Leu Val Arg Val Ser
        435                 440                 445

Ala Val Leu Thr Asn Ala Pro Tyr Ile Leu Asn Val Asp Cys Asp His
    450                 455                 460

Tyr Val Asn Asn Ser Lys Ala Val Arg Glu Ala Met Cys Ile Leu Met
465                 470                 475                 480

Asp Pro Gln Val Gly Arg Asp Val Cys Tyr Val Gln Phe Pro Gln Arg
                485                 490                 495

Phe Asp Gly Ile Asp Lys Ser Asp Arg Tyr Ala Asn Arg Asn Val Val
            500                 505                 510

Phe Phe Asp Val Asn Met Lys Gly Leu Asp Gly Ile Gln Gly Pro Val
        515                 520                 525

Tyr Val Gly Thr Gly Cys Val Phe Asn Arg Gln Ala Leu Tyr Gly Tyr
    530                 535                 540

Gly Pro Pro Ser Met Pro Ser Leu Arg Lys Arg Lys Asp Ser Ser Ser
545                 550                 555                 560

Cys Phe Ser Cys Cys Cys Pro Ser Lys Lys Lys Pro Ala Gln Asp Pro
                565                 570                 575

Ala Glu Val Tyr Arg Asp Ala Lys Arg Glu Asp Leu Asn Ala Ala Ile
            580                 585                 590

Phe Asn Leu Thr Glu Ile Asp Asn Tyr Asp Glu His Glu Arg Ser Met
        595                 600                 605

Leu Ile Ser Gln Leu Ser Phe Glu Lys Thr Phe Gly Leu Ser Ser Val
    610                 615                 620

Phe Ile Glu Ser Thr Leu Met Glu Asn Gly Gly Val Pro Glu Ser Ala
625                 630                 635                 640

Asn Ser Pro Pro Phe Ile Lys Glu Ala Ile Gln Val Ile Gly Cys Gly
                645                 650                 655

Tyr Glu Glu Lys Thr Glu Trp Gly Lys Gln Ile Gly Trp Ile Tyr Gly
            660                 665                 670

Ser Val Thr Glu Asp Ile Leu Ser Gly Phe Lys Met His Cys Arg Gly
        675                 680                 685

Trp Arg Ser Ile Tyr Cys Met Pro Val Arg Pro Ala Phe Lys Gly Ser
    690                 695                 700

Ala Pro Ile Asn Leu Ser Asp Arg Leu His Gln Val Leu Arg Trp Ala
705                 710                 715                 720

Leu Gly Ser Val Glu Ile Phe Phe Ser Arg His Cys Pro Leu Trp Tyr
                725                 730                 735

Gly Phe Gly Gly Gly Arg Leu Lys Trp Leu Gln Arg Leu Ala Tyr Ile
            740                 745                 750

Asn Thr Ile Val Tyr Pro Phe Thr Ser Leu Pro Leu Ile Ala Tyr Cys
        755                 760                 765

Thr Ile Pro Ala Val Cys Leu Leu Thr Gly Lys Phe Ile Ile Pro Thr
    770                 775                 780

Leu Ser Asn Leu Ala Ser Met Leu Phe Leu Gly Leu Phe Ile Ser Ile
785                 790                 795                 800

Ile Val Thr Ala Val Leu Glu Leu Arg Trp Ser Gly Val Ser Ile Glu
```

-continued

```
                    805                 810                 815
Asp Leu Trp Arg Asn Glu Gln Phe Trp Val Ile Gly Gly Val Ser Ala
                820                 825                 830

His Leu Phe Ala Val Phe Gln Gly Phe Leu Lys Met Leu Ala Gly Ile
            835                 840                 845

Asp Thr Asn Phe Thr Val Thr Ala Lys Ala Ala Glu Asp Ala Glu Phe
        850                 855                 860

Gly Glu Leu Tyr Met Val Lys Trp Thr Thr Leu Leu Ile Pro Pro Thr
865                 870                 875                 880

Thr Leu Leu Ile Ile Asn Met Ser Gly Cys Ala Gly Phe Ser Asp Ala
                885                 890                 895

Leu Asn Lys Gly Tyr Glu Ala Trp Gly Pro Leu Phe Gly Lys Val Phe
            900                 905                 910

Phe Ala Phe Trp Val Ile Leu His Leu Tyr Pro Phe Leu Lys Gly Leu
        915                 920                 925

Met Gly Arg Gln Asn Leu Thr Pro Thr Ile Val Val Leu Trp Ser Val
    930                 935                 940

Leu Leu Ala Ser Val Phe Ser Leu Val Trp Val Lys Ile Asn Pro Phe
945                 950                 955                 960

Val Asn Lys Val Asp Asn Thr Leu Val Ala Glu Thr Cys Ile Ser Ile
                965                 970                 975

Asp Cys

<210> SEQ ID NO 3
<211> LENGTH: 1010
<212> TYPE: DNA
<213> ORGANISM: Populus tremuloides
<220> FEATURE:
<221> NAME/KEY: CDS
<222> LOCATION: (841)..(1008)
<220> FEATURE:
<221> NAME/KEY: misc_feature
<223> OTHER INFORMATION: 5' flanking region of PtCelA coding sequence

<400> SEQUENCE: 3
gaattcgccc ttttgaattc aggagacgat agtttccggt tcgttgaatg gctttgttca      60
cttctggtct agcaatttgc aaaagaagtt acaaaacaaa tgcatattat gtaaatttaa     120
caagagatgg gttctatggt cacttattta tgcccatcat ttgttctggg gttactcttt     180
atagtctgat tcgaagttgc aaactgccgt ttctggtatt gcaattatgt agccataaac     240
tgttaatcct gtagctatta gcggaccaac aaccagatat acgggatcag cgtcgtaaaa     300
gagatctcca ttctacgttt ctttctaatt tttccgtttc agtgagagaa ttaccctgat     360
acattgacat gatgattgat gattatggga accattccga tgttagacac gagaccatct     420
ggatcctgcc agttttcagt tcacatggca tctcagccca agatcatgtg tttatacgcc     480
taatgacttg tattgaaagt ttggtaagtt gaagatgtgc tctgcccaac agaaaccttc     540
cttaaatttc cagcaaatct ttcaaacttg gccttacacc ccgaaaatag acgtgcttct     600
acttgggttc ttggaaacca tgcaccaacc gccataccccc accaacccac caccctcaac     660
cttctcttcg ccattacaaa aatgtcagta ccaccctctg aaagacacca acacaccctaa    720 gctttggtta gggtatttga tataaaaaca aggccaaaac aaaagattgg aaggaagcag     780
aggaagaccc tcttgaaaga attgaagttg taaagagctg gtaaagtggt aataagcaag     840 atg atg gaa tct ggg gct cct ata tgc cat acc tgt ggt gaa cag gtg        888
Met Met Glu Ser Gly Ala Pro Ile Cys His Thr Cys Gly Glu Gln Val
1               5                   10                  15
```

```
ggg cat gat gca aat ggg gag cta ttt gtg gct tgc cat gag tgt agc    936
Gly His Asp Ala Asn Gly Glu Leu Phe Val Ala Cys His Glu Cys Ser
            20                  25                  30 tat ccc atg tgc aag tct tgt ttc gag ttt gaa atc aaa gag ggc cgg    984
Tyr Pro Met Cys Lys Ser Cys Phe Glu Phe Glu Ile Lys Glu Gly Arg
        35                  40                  45 aaa gtt tgc ttg cgg tgt ggc tcg ag                                1010
Lys Val Cys Leu Arg Cys Gly Ser
    50                  55

<210> SEQ ID NO 4
<211> LENGTH: 3444
<212> TYPE: DNA
<213> ORGANISM: Arabidopsis thaliana

<400> SEQUENCE: 4
```

| | | | | | |
|---|---|---|---|---|---|
| gcggccgcgg | ttaatcgccg | gttctcacaa | caggaatgag | tttgtcctca | ttaatgccga | 60 |
| tgagaatgcc | cgaataagat | cagtccaaga | gctgagtgga | cagacatgtc | aaatctgcag | 120 |
| agatgagatc | gaattgactg | ttgatggaga | accgtttgtg | gcatgtaacg | aatgtgcatt | 180 |
| ccctgtgtgt | agaccttgct | atgagtacga | aagacgagaa | ggcaatcaag | cttgtccaca | 240 |
| gtgcaaaacc | cgtttcaaac | gtcttaaagg | aagtccaaga | gttgaaggtg | atgaagagga | 300 |
| agatgacatt | gatgatttag | acaatgagtt | tgagtatgga | aataatggga | ttggatttga | 360 |
| tcaggtttct | gaaggtatgt | caatctctcg | tcgcaactcc | ggtttcccac | aatctgattt | 420 |
| ggattcagct | ccacctggct | ctcagattcc | attgctgact | acggcgacg | aggacgttga | 480 |
| gatttcttct | gatagacatg | ctcttattgt | tcctccttca | cttggtggtc | atggcaatag | 540 |
| agttcatcct | gtttctcttt | ctgacccgac | cgtggctgca | catcgaaggc | tgatggtacc | 600 |
| tcagaaagat | cttgcggttt | atggttatgg | aagtgtcgct | tggaaagatc | ggatggagga | 660 |
| atggaagaga | aagcagaatg | agaaacttca | ggttgttagg | catgaaggag | atcctgattt | 720 |
| tgaagatggt | gatgatgctg | attttccaat | gatggatgag | ggaaggcagc | cattgtctat | 780 |
| gaagatacca | atcaaatcga | gcaagataaa | tccttaccgg | atgttaattg | tgctacgtct | 840 |
| tgtgattctt | ggtctcttct | ttcactaccg | tattcttcac | cccgtcaaag | atgcatatgc | 900 |
| tttgtggctt | atttctgtta | tatgtgagat | atggttttgct | gtttcatggg | ttcttgatca | 960 |
| gttccctaaa | tggtacccta | tcgagcgaga | aacgtacttg | gaccgactct | cattaagata | 1020 |
| tgagaaagaa | gggaaaccgt | cgggactatc | ccctgtggat | gtatttgtta | gtacagtgga | 1080 |
| tccattgaaa | gagcctccgc | ttattactgc | aaatactgtc | ttgtctattc | ttgctgttga | 1140 |
| ttatcctgtc | gataaggttg | cttgttacgt | atctgatgat | ggtgctgcta | tgcttacttt | 1200 |
| cgaagctctt | tctgagaccg | ctgaattcgc | aaggaaatgg | gttcctttct | gcaagaaata | 1260 |
| ttgtattgag | cctcgtgctc | ccgaatggta | tttctgccat | aaaatggact | acttgaagaa | 1320 |
| taaagttcat | cccgcatttg | ttagggagcg | gcgagccatg | aagagagatt | atgaagaatt | 1380 |
| caaagtaaag | atcaatgctt | tagtagcaac | agcacagaaa | gtgcctgagg | atggttggac | 1440 |
| tatgcaagac | ggtacacctt | ggcccggtaa | tagtgtgcga | gatcatcctg | gcatgattca | 1500 |
| ggtcttcctt | ggaagtgacg | gtgttcgtga | tgtcgaaaac | aacgagttgc | ctcgattagt | 1560 |
| ttacgtttct | cgtgagaaga | gacccggatt | tgatcaccat | aagaaggctg | gagctatgaa | 1620 |
| ttccctgata | cgagtctctg | gggttctatc | aaatgctcct | taccttctga | atgtcgattg | 1680 |
| tgatcactac | atcaacaata | gcaaagctct | tagagaagca | atgtgtttca | tgatggatcc | 1740 |

```
tcagtcagga aagaaaatct gttatgttca gttccctcaa aggttcgatg ggattgatag    1800
gcacgatcga tactcaaatc gcaatgttgt gttctttgat atcaatatga aaggtttgga    1860
tgggctacaa gggcctatat acgtcggtac aggttgtgtt ttcaggaggc aagcgcttta    1920
cggatttgat gcaccgaaga agaagaaggg cccacgtaag acatgcaatt gctggccaaa    1980
atggtgtctc ctatgttttg gttcaagaaa gaatcgtaaa gcaaagacag tggctgcgga    2040
taagaagaag aagaataggg aagcgtcaaa gcagatccac gcattagaaa atatcgaaga    2100
gggccgcggt cataaagttc ttaacgtaga acagtcaacc gaggcaatgc aaatgaagtt    2160
gcagaagaaa tatgggcagt ctcctgtatt tgttgcatct gcgcgtctgg agaatggtgg    2220
gatggctaga aacgcaagcc cggcttgtct gcttaaagaa gccatccaag tcattagtcg    2280
cggatatgaa gataaaactg aatggggaaa agagattggg tggatctatg gttctgttac    2340
cgaagatatt cttacgggtt ctaagatgca ttctcatggt tggagacatg tttattgtac    2400
accaaagtta gcggctttca aaggatcagc tccaatcaat ctttcggatc gtctccatca    2460
agttcttcga tgggcgcttg ggtcggttga gattttcttg agtaggcatt gtcctatttg    2520
gtatggttat ggaggtgggt tgaaatggct tgagcggttg tcctacatta actctgtggt    2580
ttaccgtgga acctctctac cgctcatcgt ttactgttct ctccctgcca tctgtcttct    2640
cactggaaaa ttcatcgttc ccgagattag caactatgcg agtatcctct tcatggcgct    2700
cttctcgtcg attgcaataa cgggtattct cgagatgcaa tggggcaaag ttgggatcga    2760
tgattggtgg agaaacgaac agttttgggt cattggaggt gtttctgcgc atctgtttgc    2820
tctcttccaa ggtctcctca aggttcttgc tggtgtcgac actaacttca cagtcacatc    2880
aaaagcagct gatgatggag agttctctga cctttacctc ttcaaatgga cttcacttct    2940
catccctcca atgactctac tcatcataaa cgtcattgga gtcatagtcg gagtctctga    3000
tgccatcagc aatggatacg actcgtgggg accgcttttc ggaagactgt tctttgcact    3060
ttgggtcatc attcatcttt acccgttcct taaaggtttg cttgggaaac aagatagaat    3120
gccaaccatt attgtcgtct ggtccatcct cctggcctcg attcttacac ttctttgggt    3180
ccgggttaat ccgtttgtgg cgaaaggcgg tcctattctc gagatctgtg gtttagactg    3240
cttgtgattc gattgaccgg tggatgggtt ggtgaaaaag gtttaattcc cacggatcaa    3300
agagaggtaa gagagatatt gttttacctc taaaagactc cttcattgtg ttcattagat    3360
gatgaaaaat gaaagaaaa agaagattta attttgttac gagaattgtt atttttgcaa    3420
gaatgtgttg tagatagcgg ccgc                                          3444
```

<210> SEQ ID NO 5
<211> LENGTH: 1080
<212> TYPE: PRT
<213> ORGANISM: Arabidopsis thaliana
<220> FEATURE:
<221> NAME/KEY: misc_feature
<223> OTHER INFORMATION: cellulose synthase

<400> SEQUENCE: 5

Arg Pro Arg Leu Ile Ala Gly Ser His Asn Arg Asn Glu Phe Val Leu
 1               5                  10                  15

Ile Asn Ala Asp Glu Asn Ala Arg Ile Arg Ser Val Gln Glu Leu Ser
            20                  25                  30

Gly Gln Thr Cys Gln Ile Cys Arg Asp Glu Ile Glu Leu Thr Val Asp
        35                  40                  45

Gly Glu Pro Phe Val Ala Cys Asn Glu Cys Ala Phe Pro Val Cys Arg

-continued

```
            50                    55                      60
Pro Cys Tyr Glu Tyr Arg Arg Glu Gly Asn Gln Ala Cys Pro Gln
 65                      70                      75                  80

Cys Lys Thr Arg Phe Lys Arg Leu Lys Gly Ser Pro Arg Val Glu Gly
                     85                      90                      95

Asp Glu Glu Glu Asp Ile Asp Asp Leu Asp Asn Glu Phe Glu Tyr
                100                     105                     110

Gly Asn Asn Gly Ile Gly Phe Asp Gln Val Ser Glu Gly Met Ser Ile
                115                     120                     125

Ser Arg Arg Asn Ser Gly Phe Pro Gln Ser Asp Leu Asp Ser Ala Pro
130                     135                     140

Pro Gly Ser Gln Ile Pro Leu Leu Thr Tyr Gly Asp Glu Asp Val Glu
145                     150                     155                 160

Ile Ser Ser Asp Arg His Ala Leu Ile Val Pro Pro Ser Leu Gly Gly
                165                     170                     175

His Gly Asn Arg Val His Pro Val Ser Leu Ser Asp Pro Thr Val Ala
                180                     185                     190

Ala His Arg Arg Leu Met Val Pro Gln Lys Asp Leu Ala Val Tyr Gly
                195                     200                     205

Tyr Gly Ser Val Ala Trp Lys Asp Arg Met Glu Glu Trp Lys Arg Lys
                210                     215                     220

Gln Asn Glu Lys Leu Gln Val Val Arg His Glu Gly Asp Pro Asp Phe
225                     230                     235                 240

Glu Asp Gly Asp Asp Ala Asp Phe Pro Met Met Asp Glu Gly Arg Gln
                245                     250                     255

Pro Leu Ser Met Lys Ile Pro Ile Lys Ser Ser Lys Ile Asn Pro Tyr
                260                     265                     270

Arg Met Leu Ile Val Leu Arg Leu Val Ile Leu Gly Leu Phe Phe His
                275                     280                     285

Tyr Arg Ile Leu His Pro Val Lys Asp Ala Tyr Ala Leu Trp Leu Ile
                290                     295                     300

Ser Val Ile Cys Glu Ile Trp Phe Ala Val Ser Trp Val Leu Asp Gln
305                     310                     315                 320

Phe Pro Lys Trp Tyr Pro Ile Glu Arg Glu Thr Tyr Leu Asp Arg Leu
                325                     330                     335

Ser Leu Arg Tyr Glu Lys Glu Gly Lys Pro Ser Gly Leu Ser Pro Val
                340                     345                     350

Asp Val Phe Val Ser Thr Val Asp Pro Leu Lys Glu Pro Pro Leu Ile
                355                     360                     365

Thr Ala Asn Thr Val Leu Ser Ile Leu Ala Val Asp Tyr Pro Val Asp
                370                     375                     380

Lys Val Ala Cys Tyr Val Ser Asp Asp Gly Ala Ala Met Leu Thr Phe
385                     390                     395                 400

Glu Ala Leu Ser Glu Thr Ala Glu Phe Ala Arg Lys Trp Val Pro Phe
                405                     410                     415

Cys Lys Lys Tyr Cys Ile Glu Pro Arg Ala Pro Glu Trp Tyr Phe Cys
                420                     425                     430

His Lys Met Asp Tyr Leu Lys Asn Lys Val His Pro Ala Phe Val Arg
                435                     440                     445

Glu Arg Arg Ala Met Lys Arg Asp Tyr Glu Glu Phe Lys Val Lys Ile
                450                     455                     460

Asn Ala Leu Val Ala Thr Ala Gln Lys Val Pro Glu Asp Gly Trp Thr
465                     470                     475                 480
```

```
Met Gln Asp Gly Thr Pro Trp Pro Gly Asn Ser Val Arg Asp His Pro
                485                 490                 495
Gly Met Ile Gln Val Phe Leu Gly Ser Asp Gly Val Arg Asp Val Glu
            500                 505                 510
Asn Asn Glu Leu Pro Arg Leu Tyr Val Ser Arg Glu Lys Arg Pro
        515                 520                 525
Gly Phe Asp His His Lys Lys Ala Gly Ala Met Asn Ser Leu Ile Arg
    530                 535                 540
Val Ser Gly Val Leu Ser Asn Ala Pro Tyr Leu Leu Asn Val Asp Cys
545                 550                 555                 560
Asp His Tyr Ile Asn Asn Ser Lys Ala Leu Arg Glu Ala Met Cys Phe
                565                 570                 575
Met Met Asp Pro Gln Ser Gly Lys Lys Ile Cys Tyr Val Gln Phe Pro
            580                 585                 590
Gln Arg Phe Asp Gly Ile Asp Arg His Asp Arg Tyr Ser Asn Arg Asn
        595                 600                 605
Val Val Phe Phe Asp Ile Asn Met Lys Gly Leu Asp Gly Leu Gln Gly
    610                 615                 620
Pro Ile Tyr Val Thr Gly Cys Val Phe Arg Arg Gln Ala Leu Tyr Gly
625                 630                 635                 640
Phe Asp Ala Pro Lys Lys Lys Gly Pro Arg Lys Thr Cys Asn Cys
                645                 650                 655
Trp Pro Lys Trp Cys Leu Leu Cys Phe Gly Ser Arg Lys Asn Arg Lys
            660                 665                 670
Ala Lys Thr Val Ala Ala Asp Lys Lys Lys Asn Arg Glu Ala Ser
        675                 680                 685
Lys Gln Ile His Ala Leu Glu Asn Ile Glu Glu Gly Arg Gly His Lys
    690                 695                 700
Val Leu Asn Val Glu Gln Ser Thr Glu Ala Met Gln Met Lys Leu Gln
705                 710                 715                 720
Lys Lys Tyr Gly Gln Ser Pro Val Phe Val Ala Ser Ala Arg Leu Glu
                725                 730                 735
Asn Gly Gly Met Ala Arg Asn Ala Ser Pro Ala Cys Leu Leu Lys Glu
            740                 745                 750
Ala Ile Gln Val Ile Ser Arg Gly Tyr Glu Asp Lys Thr Glu Trp Gly
        755                 760                 765
Lys Glu Ile Gly Trp Ile Tyr Gly Ser Val Thr Glu Asp Ile Leu Thr
    770                 775                 780
Gly Ser Lys Met His Ser His Gly Trp Arg His Val Tyr Cys Thr Pro
785                 790                 795                 800
Lys Leu Ala Ala Phe Lys Gly Ser Ala Pro Ile Asn Leu Ser Asp Arg
                805                 810                 815
Leu His Gln Val Leu Arg Trp Ala Leu Gly Ser Val Glu Ile Phe Leu
            820                 825                 830
Ser Arg His Cys Pro Ile Trp Tyr Gly Tyr Gly Gly Gly Leu Lys Trp
        835                 840                 845
Leu Glu Arg Leu Ser Tyr Ile Asn Ser Val Val Tyr Pro Trp Thr Ser
    850                 855                 860
Leu Pro Leu Ile Val Tyr Cys Ser Leu Pro Ala Ile Cys Leu Leu Thr
865                 870                 875                 880
Gly Lys Phe Ile Val Pro Glu Ile Ser Asn Tyr Ala Ser Ile Leu Phe
                885                 890                 895
```

-continued

```
Met Ala Leu Phe Ser Ser Ile Ala Ile Thr Gly Ile Leu Glu Met Gln
            900                 905                 910

Trp Gly Lys Val Gly Ile Asp Asp Trp Trp Arg Asn Glu Gln Phe Trp
        915                 920                 925

Val Ile Gly Gly Val Ser Ala His Leu Phe Ala Leu Phe Gln Gly Leu
    930                 935                 940

Leu Lys Val Leu Ala Gly Val Asp Thr Asn Phe Thr Val Thr Ser Lys
945                 950                 955                 960

Ala Ala Asp Asp Gly Glu Phe Ser Asp Leu Tyr Leu Phe Lys Trp Thr
                965                 970                 975

Ser Leu Leu Ile Pro Pro Met Thr Leu Leu Ile Ile Asn Val Ile Gly
            980                 985                 990

Val Ile Val Gly Val Ser Asp Ala Ile Ser Asn Gly Tyr Asp Ser Trp
        995                 1000                1005

Gly Pro Leu Phe Gly Arg Leu Phe Ala Leu Trp Val Ile Ile His
    1010                1015                1020

Leu Tyr Pro Phe Leu Lys Gly Leu Leu Gly Lys Gln Asp Arg Met Pro
1025                1030                1035                1040

Thr Ile Ile Val Val Trp Ser Ile Leu Leu Ala Ser Ile Leu Thr Leu
                1045                1050                1055

Leu Trp Val Arg Val Asn Pro Phe Val Ala Lys Gly Gly Pro Ile Leu
            1060                1065                1070

Glu Ile Cys Gly Leu Asp Cys Leu
    1075                1080

<210> SEQ ID NO 6
<211> LENGTH: 56
<212> TYPE: PRT
<213> ORGANISM: Populus tremuloides

<400> SEQUENCE: 6

Met Met Glu Ser Gly Ala Pro Ile Cys His Thr Cys Gly Glu Gln Val
1               5                   10                  15

Gly His Asp Ala Asn Gly Glu Leu Phe Val Ala Cys His Glu Cys Ser
            20                  25                  30

Tyr Pro Met Cys Lys Ser Cys Phe Glu Phe Glu Ile Lys Glu Gly Arg
        35                  40                  45

Lys Val Cys Leu Arg Cys Gly Ser
    50                  55

<210> SEQ ID NO 7
<211> LENGTH: 5
<212> TYPE: PRT
<213> ORGANISM: Unknown
<220> FEATURE:
<223> OTHER INFORMATION: concensus sequence

<400> SEQUENCE: 7

Gln Val Leu Arg Trp
1               5
```

CELLULOSE SYNTHASE ENCODING POLYNUCLEOTIDES AND USES THEREOF

CROSS-REFERENCE TO RELATED APPLICATIONS

This application claims the benefit of U.S. Provisional Patent Application Ser. No. 60/135,280 filed 21 May, 1999.

STATEMENT REGARDING FEDERALLY SPONSORED RESEARCH OR DEVELOPMENT

Not Applicable

FIELD OF THE INVENTION

This invention relates to polynucleotide molecules encoding cellulose synthase, promoters of cellulose synthase and cellulose synthase polypeptides, methods for genetically altering cellulose and lignin biosynthesis, and methods for improving strength properties of juvenile wood and fiber in trees. The invention further relates to methods for identifying regulatory elements in a cellulose synthase promoter and transcription factors that bind to such regulatory elements, and to methods for augmenting expression of polynucleotides operably linked to a cellulose synthase promoter.

BACKGROUND OF THE INVENTION

Lignin and cellulose are the two major building blocks of plant cell walls that provide mechanical strength and rigidity. In plants, and especially in trees, these two organic materials exist in a dynamic equilibrium conferring mechanical strength, water transporting ability and protection from biotic and abiotic environmental stresses. Normally, oven-dry wood contains 30 to 50% cellulose, 20 to 30% lignin and 20 to 30% hemicellulose (Higuchi, 1997).

Proportions of lignin and cellulose are known to change with variation in the natural environment. For example, during the development of compression wood in conifers, the percentage of lignin increases from 30 to 40%, and cellulose content proportionally decreases from 40 to 30% (Timmell, 1986). Conversely, in angiosperm tension wood the percentage of cellulose increases from 30 to 40%, while lignin content decreases from 30 to 20% (Timmell, 1986).

It was recently discovered that the genetic down-regulation of a key tissue-specific enzyme from the lignin biosynthesis pathway, 4CL, results in reduction of lignin content by up to 45% in transgenic aspen trees (Hu et al., 1999). This down-regulation is also associated with a 15% increase in the cellulose content. If the converse were true, i.e., that increasing cellulose content by genetic up-regulation of cellulose biosynthesis results in reduction of lignin content, then the pulp yield could be increased. This would allow tremendous savings in chemical and energy costs during pulping because, for example, lignin must be degraded and removed during the pulping process.

Cellulose is a linear glucan consisting of β-D-1,4-linked glucose residues. It is formed by a cellulose synthase enzyme which catalyzes assembly of UDP-glucose units in plasma membrane complexes known as "particle rosettes" (Delmer and Amor, 1995). Cellulose synthase is thought to be anchored to the membrane by eight transmembrane binding domains to form the basis of the cellulose biosynthesis machinery in the plant cell wall (Pear et al., 1996).

In higher plants, the glucan chains in cellulose microfibrils of primary and secondary cell walls are different in their degree of polymerization (Brown et al., 1996). For example, secondary cell walls are known to contain cellulose having a high degree of polymerization, while in primary cell walls the degree of polymerization is lower. In another example, woody cell walls suffering from tension stress produce tension wood on the upper side of a bent angiosperm tree in response to the stress. In these cells, there are elevated quantities of cellulose which have very high crystallinity. The formation of highly crystalline cellulose is important to obtain a higher tensile strength of the wood fiber. Woody cell walls located at the under side of the same stem experience a compression stress, but do not produce highly crystalline cellulose. Such variation in the degree of polymerization in cell walls during development is believed to be due to different types of cellulose synthases for organizing glucose units into different paracrystalline arrays (Haigler and Blanton, 1996). Therefore, it would be advantageous to determine the molecular basis for the synthesis of highly crystalline cellulose so that higher yields of wood pulp having superior strength properties can be obtained from transgenic trees. Production of highly crystalline cellulose in transgenic trees would also markedly improve the mechanical strength properties of juvenile wood formed in normal trees. This would be a great benefit to the industry because juvenile wood is generally undesirable for solid wood applications because it has inferior mechanical properties.

Since the deposition of cellulose and lignin in trees is regulated in a compensatory fashion, genetic augmentation of cellulose biosynthesis might have a repressive effect on lignin deposition. Since the degree of polymerization and crystallinity may depend upon the type of cellulose synthase incorporated in the cellulose biosynthesis machinery, the expression of heterologous cellulose synthase or a UDP-glucose binding region thereof (e.g., sweetgum protein expression in loblolly pine), could increase the quality of cellulose in transgenic plants. Over-expression of a heterologous cellulose synthase may also increase cellulose quantity in transgenic plants. Thus, genetic engineering of cellulose biosynthesis can provide a strategy to augment cellulose quality and quantity, while reducing lignin content in transgenic plants.

A better understanding of the biochemical processes that lead to wood formation would enable the pulp and paper industries to more effectively use genetic engineering as a tool to meet the increasing demands for wood from a decreasing production area. With this objective, many xylem-specific genes, including most lignin biosynthesis genes, have been isolated from developing xylem tissues of various plants including tree species (Ye and Varner, 1993; Fukuda, 1996; Whetten et al., 1998). Genes regulating cellulose biosynthesis in crop plants (Pear et al., 1996 and Arioli et al., 1998), versus in trees, have also been isolated. However, isolation of tree genes which are directly involved in cellulose biosynthesis has remained a great challenge.

For more than 30 years, no gene encoding higher plant cellulose synthase (CelA) was identified. Recently, Pear et al. (1996) isolated the first putative higher plant CelA cDNA, GhCelA (GenBank No. GHU58283), by searching for UDP-glucose binding sequences in a cDNA library prepared from cotton fibers having active secondary wall cellulose synthesis. GhCelA was considered to encode a cellulose synthase catalytic subunit because it is highly expressed in cotton fibers, actively synthesizes secondary wall cellulose, contains eight transmembrane domains, binds UDP-glucose, and contains two other domains unique to plants.

Recently, Arioli et al. (1998) cloned a CelA homolog, RSW1 (radial swelling) (GenBank No. AF027172), from *Arabidopsis* by chromosome walking to a defective locus of a temperature sensitive cellulose-deficient mutant. Complementation of the RSW1 mutant with a wild type full-length genomic RSW1 clone restored the normal phenotype. This complementation provided the first genetic proof that a plant CelA gene encodes a catalytic subunit of cellulose synthase and functions in the biosynthesis of cellulose microfibrils. The full-length *Arabidopsis* RSW1 represents the only known, currently available cellulose synthase cDNA available for further elucidating cellulose biosynthesis in transgenic systems (Wu et al., 1998).

The discovery of the RSW1 gene substantiated the belief that the assembly of a cellulose synthase into the plasma membrane is required for functional cellulose biosynthetic machinery and for manufacturing crystalline cellulose microfibrils in plant cell walls. Most significantly, a single CelA gene, e.g. RSW1, is sufficient for the biosynthesis of cellulose microfibrils in plants, e.g. *Arabidopsis*. Thus, RSW1 is a prime target for engineering augmented cellulose formation in transgenic plants.

Since many of society's fiber, chemical and energy demands are met through the industrial-scale production of cellulose from wood, genetic engineering of the cellulose biosynthesis machinery in trees could produce higher pulp yields. This would allow greater returns on investment by pulp and paper industries. Therefore, it would be advantageous to isolate and characterize genes from trees that are involved in cellulose biosynthesis in order to improve the properties of wood.

SUMMARY OF THE INVENTION

The present invention relates to polynucleotides comprising a nucleotide sequence that encodes a cellulose synthase, regulatory sequences, including a stress-inducible promoter, of the cellulose synthase, a cellulose synthase protein or a functional domain thereof and methods for augmenting cellulose biosynthesis in plants.

Thus, in one aspect, the invention provides a polynucleotide comprising a sequence that encodes a cellulose synthase, or a polynucleotide fragment thereof, the fragment encoding a functional domain of cellulose synthase, such as a UDP-glucose binding domain. The invention also provides a cellulose synthase or a functional domain or fragment thereof, including a UDP-glucose binding domain and at least one of eight transmembrane domains. The invention further provides a cellulose synthase promoter, or a functional fragment thereof, which fragment contains one or more mechanical stress response elements (MSRE).

In another aspect, the present invention is directed to a method of improving the quality of wood by altering the quantity of cellulose in plant cells, and optionally decreasing the content of lignin in the cell. The invention also relates to a method of altering the growth or the cellulose content of a plant by expressing an exogenous polynucleotide encoding a cellulose synthase or a UDP-glucose binding domain thereof in the plant. The invention further provides a method for causing a stress-induced gene expression in a plant cell by expressing a polynucleotide of choice using a stress-inducible cellulose synthase promoter.

In yet another aspect, the invention relates to a method for determining a mechanical stress responsive element (MSRE) in a cellulose synthase promoters and a method for identifying transcription factors that binds to the MSRE.

In a further aspect, the invention provides a method for altering (increasing or decreasing) i.e., regulating, the expression of a cellulose synthase in a plant by expressing an exogenous polynucleotide encoding a transcription factor having the property of binding a positive MSRE of a cellulose synthase promoter or by expressing an antisense polynucleotide encoding a transcription factor having the property of binding a negative MSRE to block the expression of the transcription factor.

Other aspects of the invention will be appreciated by a consideration of the detailed description of the invention drawings and appended claims.

DESCRIPTION OF THE DRAWINGS

FIG. 1 represents a nucleic acid sequence encoding a cellulose synthase from *Populus tremuloides* [SEQ ID NO: 1] and the protein sequence thereof [SEQ ID NO: 2].

FIGS. 3 *a–d* (collectively referred to as FIG. 3) represent in situ localization of the cellulose synthase gene transcripts as shown in the transverse sections from second (panel a), fourth (panel b), sixth (panel c) and fifth (panel d) internode.

FIG. 4 represents a nucleic acid sequence of the 5' region of aspen cellulose synthase gene including the promoter region and the 5' portion of the coding sequence [SEQ ID NO: 3] and the peptide sequence deduced from the coding sequence [SEQ ID NO: 6].

FIGS. 5 *a–f* (collectively referred to as FIG. 5) represents a histochemical analysis (panels a–d and f) and fluorescence microscopy (panel e) of transgenic tobacco for GUS gene expression driven by a cellulose synthase promoter of the invention.

FIGS. 6 *a–d* (collectively referred to as FIG. 6) represents a histochemical analysis of GUS gene expression driven by aspen cellulose synthase promoter of the invention; tangential and longitudinal sections were harvested before bending (panel a), and 4 (panel b), 20 (panel c) and 40 (panel d) hours after bending and stained for GUS expression.

FIG. 7 represents a cDNA encoding cellulose synthase isolated from *Arabidopsis* [SEQ ID NO:4].

FIG. 8 represents an *Arabidopsis* cellulose synthase [SEQ ID NO:5] encoded by the cDNA represented in FIG. 7.

DETAILED DESCRIPTION OF THE INVENTION

Figure 2:
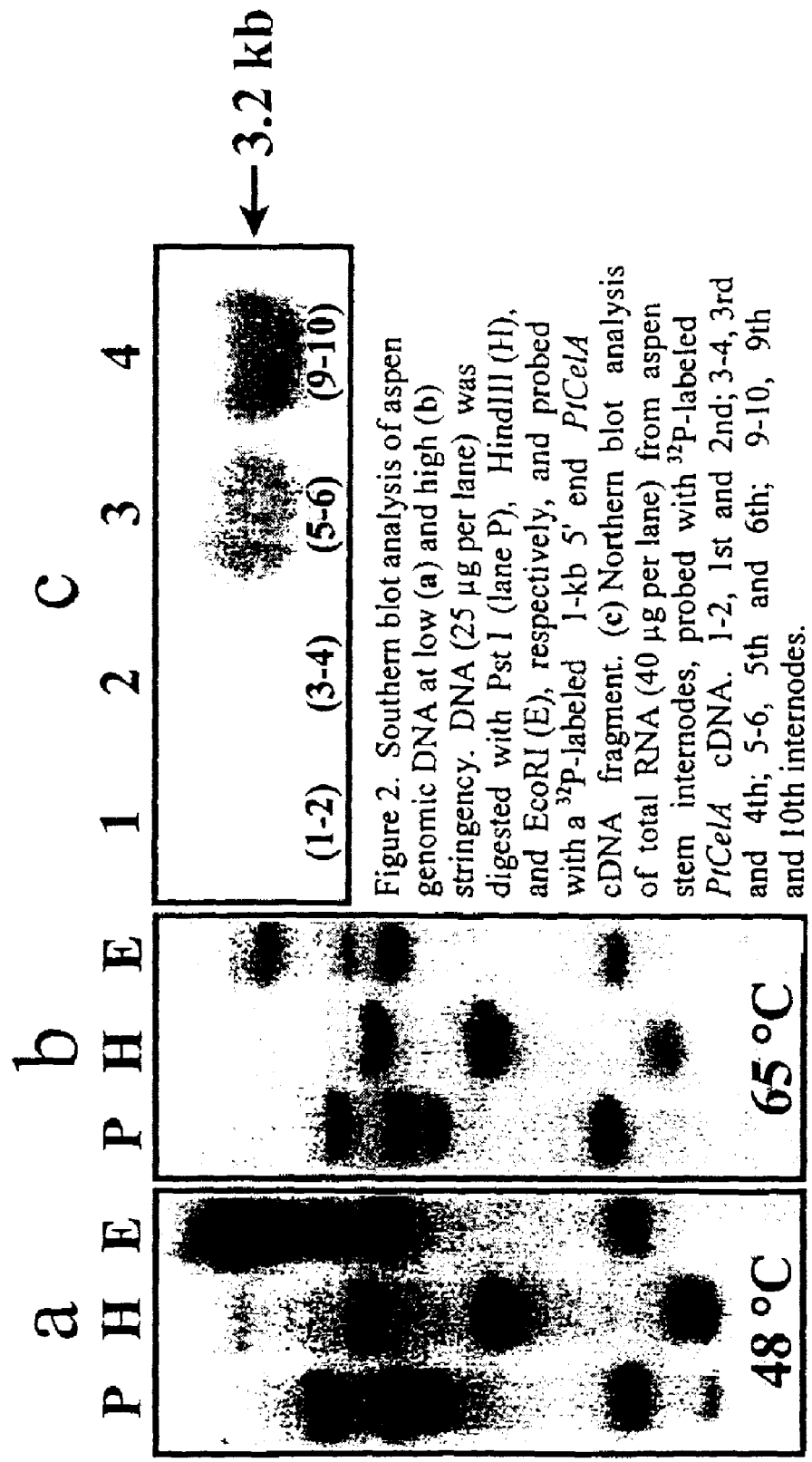
FIGS. 2 *a–c* (collectively referred to as FIG. 2) represent a Southern blot analysis of aspen genomic DNA probed with a fragment of the aspen cDNA represented in FIG. 1 under low (panel a) and high stringency conditions (panel b), and a northern blot analysis of the total aspen RNA from stem internodes using the same probe (panel c).

All patents, patent applications and references cited in this specification are hereby incorporated herein by reference in their entirety. In case of any inconsistency, the present disclosure governs.

Definitions

The terms used in this specification generally have their ordinary meanings in the art, within the context of the invention, and in the specific context where each term is used. Certain terms are discussed below, or elsewhere in the specification, to provide additional guidance to the person of skill in the art in describing the compositions and methods of the invention and how to make and use them. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

The term "plant" includes whole plants and portions of plants, including plant organs (e.g. roots, stems, leaves, etc.).

The term "angiosperm" refers to plants which produce seeds encased in an ovary. A specific example of an angiosperm is *Liquidambar styraciflua* (L.)[sweetgum].

The term "gymnosperm" refers to plants which produce naked seeds, that is, seeds which are not encased in an ovary. Specific examples of a gymnosperm include *Pinus taeda* (L.)[loblolly pine].

The term "polynucleotide" or "nucleic acid molecule" is intended to include double or single stranded genomic and cDNA, RNA, any synthetic and genetically manipulated polynucleotide, and both sense and anti-sense strands together or individually (although only sense or anti-sense stand may be represented herein). This includes single- and double-stranded molecules, i.e., DNA—DNA, DNA-RNA and RNA—RNA hybrids, as well as "protein nucleic acids" (PNA) formed by conjugating bases to an amino acid backbone. This also includes nucleic acids containing modified bases, for example thio-uracil, thio-guanine and fluoro-uracil.

An "isolated" nucleic acid molecule or polynucleotide refers to a component that is removed from its original environment (for example, its natural environment if it is naturally occurring). An isolated nucleic acid or polypeptide may contain less than about 50%, preferably less than about 75%, and most preferably less than about 90%, of the cellular components with which it was originally associated. A polynucleotide amplified using PCR so that it is sufficiently and easily distinguishable (on a gel, for example) from the rest of the cellular components is considered "isolated". The polynucleotides and polypeptides of the invention may be "substantially pure," i.e., having the highest degree of purity that can be achieved using purification techniques known in the art.

The term "hybridization" refers to a process in which a strand of nucleic acid joins with a complementary strand through base pairing. Polynucleotides are "hybridizable" to each other when at least one strand of one polynucleotide can anneal to a strand of another polynucleotide under defined stringency conditions. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarily over their entire sequence. Conditions of intermediate stringency (such as, for example, an aqueous solution of 2× SSC at 65° C.) and low stringency (such as, for example, an aqueous solution of 2× SSC at 55° C.), require correspondingly less overall complementarily between the hybridizing sequences. (1× SSC is 0.15 M NaCl, 0.015 M Na citrate.) As used herein, the above solutions and temperatures refer to the probe-washing stage of the hybridization procedure. The term "a polynucleotide that hybridizes under stringent (low, intermediate) conditions" is intended to encompass both single and double-stranded polynucleotides although only one strand will hybridize to the complementary strand of another polynucleotide.

A "sequence-conservative variant" is a polynucleotide that contains a change of one or more nucleotides in a given codon position, as compared with another polynucleotide, but the change does not result in any alteration in the amino acid encoded at that position.

A "function-conservative variant" is a polypeptide (or a polynucleotide encoding the polypeptide) having a given amino acid residue that has been changed without altering the overall conformation and function of the polypeptide, including, but not limited to, replacement of an amino acid with one having similar physico-chemical properties (such as, for example, acidic, basic, hydrophobic, and the like). Amino acids having similar physico-chemical properties are well known in the art. For example, arginine, histidine and lysine are hydrophilic-basic amino acids and may be interchangeable. Similarly, isoleucine, a hydrophobic amino acid, may be replaced with leucine, methionine or valine. Sequence-and function-conservative variants are discussed in greater detail below with respect to degeneracy of the genetic code.

A "functional domain" or a "functional fragment" refers to any region or portion of a protein or polypeptide or polynucleotide which is a region or portion of a larger protein or polynucleotide, the region or portion having the specific activity or specific function attributable to the larger protein or polynucleotide, e.g., a functional domain of cellulose synthase is the UDP-glucose binding domain.

The term "% identity" refers to the percentage of the nucleotides/amino acids of one polynucleotide/polypeptide that are identical to the nucleotides/amino acids of another sequence of polynucleotide/polypeptide as identified by program GAP from Genetics Computer Group Wisconsin (GCG) package (version 9.0) (Madison, Wis.). GAP uses the algorithm of Needleman and Wunsch (J. Mol. Biol. 48: 443–453, 1970) to find the alignment of two complete sequences that maximizes the number of matches and minimizes the number of gaps. When parameters required to run the above algorithm are not specified, the default values offered by the program are contemplated. The following parameters are used by the GCG program GAP as default values (for polynucleotides): gap creation penalty:50; gap extension penalty:3; scoring matrix: nwsgapdna.cpm (local data file).

The "% similarity" or "% homology" between two polypeptide sequences is a function of the number of similar positions shared by two sequences on the basis of the scoring matrix used divided by the number of positions compared and then multiplied by 100. This comparison is made when two sequences are aligned (by introducing gaps if needed) to determine maximum homology. PowerBlast program, implemented by the National Center for Biotechnology Information, can be used to compute optimal, gapped alignments. GAP program from Genetics Computer Group Wisconsin package (version 9.0) (Madison, Wis.) can also be used. GAP uses the algorithm of Needleman and Wunsch (J Mol Biol 48: 443–453, 1970) to find the alignment of two complete sequences that maximizes the number of matches and minimizes the number of gaps. When parameters required to run the above algorithm are not specified, the default values offered by the program are contemplated. The following parameters are used by the GCG program GAP as default values (for polypeptides): gap creation penalty:12; gap extension penalty:4; scoring matrix:Blosum62.cpm (local data file).

The term "oligonucleotide" refers to a nucleic acid, generally of at least 10, preferably at least 15, and more preferably at least 20 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of CelA, or to detect the presence of nucleic acids encoding CelA. In a further embodiment, an oligonucleotide of the invention can form a triple helix with a CelA DNA molecule. In still another embodiment, a library of oligonucleotides arranged on a solid support, such as a silicon wafer or chip, can be used to detect various polymorphisms of interest. Generally, oligonucleotides are prepared synthetically, preferably on a nucleic acid synthesizer. Accordingly, oligonucleotides can be prepared with non-naturally occurring phosphoester analog bonds, such as thioester bonds, etc.

The term "coding sequence" refers to that portion of the gene that contains the information for encoding a polypeptide. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences.

A "promoter" is a polynucleotide containing elements (e.g., a TATA box) which are capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Examples of promoters that can be used in the present invention include PtCelAP, 4CL-1 and 35S.

The term "constitutive promoter" refers to a promoter which typically, does not require positive regulatory proteins to activate expression of an associated coding sequence, i.e., a constitutive promoter maintains some basal level of expression. A constitutive promoter is commonly used in creation of an expression cassette. An example of a constitutive promoter are 35S CaMV (Cauliflower Mosaic Virus), available from Clonetech, Palo Alto, Calif.

The term "inducible promoter" refers to the promoter which requires a positive regulation to activate expression of an associated coding sequence. An example of such a promoter is a stress-inducible cellulose synthase promoter from aspen described herein.

A coding sequence is "under the control" of transcriptional and translational control sequences in a cell when RNA polymerase transcribes the coding sequence into mRNA, which is then trans-RNA spliced and translated into the protein encoded by the coding sequence.

A "vector" is a recombinant nucleic acid construct, such as plasmid, phage genome, virus genome, cosmid, or artificial chromosome to which a polynucleotide of the invention may be attached. In a specific embodiment, the vector may bring about the replication of the attached segment, e.g., in the case of a cloning vector.

The term "expression cassette" refers to a polynucleotide which contains both a promoter and a protein coding sequence such that expression of a given protein is achieved upon insertion of the expression cassette into a cell.

A cell has been "transfected" by exogenous or heterologous polynucleotide when such polynucleotide has been introduced inside the cell. A cell has been "transformed" by exogenous or heterologous polynucleotide when the transfected polynucleotide effects a phenotypic change. Preferably, the transforming polynucleotide should be integrated (covalently linked) into chromosomal DNA making up the genome of the cell.

"Exogenous" refers to biological material, such as a polynucleotide or protein, that has been isolated from a cell and is then introduced into the same or a different cell. For example, a polynucleotide encoding a cellulose synthase of the invention can be cloned from xylem cells of a particular species of tree, inserted into a plasmid and reintroduced into xylem cells of the same or different species. The species thus contains an exogenous cellulose synthase polynucleotide.

"Heterologous polynucleotide" refers to an exogenous polynucleotide not naturally occurring in the cell into which it is introduced.

"Homologous polynucleotide" refers to an exogenous polynucleotide that naturally exists in the cells into which it is introduced.

The present invention relates to isolation and characterization of polynucleotides encoding cellulose synthases from plants, especially trees, including full length or naturally occurring forms of cellulose synthases, functional domains, promoters and regulatory elements. Therefore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; B. Perbal, *A Practical Guide To Molecular Cloning* (1984); F. M. Ausubel et al. (eds.), *Current Protocols in Molecular Biology*, John Wiley & Sons, Inc. (1994).

The present invention relates to a novel, full-length cellulose synthase gene (CelA), a novel stress inducible promoter of cellulose synthases (CelAP), and cellulose synthase proteins from trees, including UDP-glucose catalytic domains thereof. The invention enables the development of transgenic tree varieties having increased cellulose content, decreased lignin content and, therefore, improved wood fiber characteristics. Production of increased cellulose quantity and quality in multiple varieties of commercially relevant, transgenic forest tree species in operational production scenarios are further contemplated. The invention further provides a new experimental system for study of CelA gene expression and function in trees.

Polynucleotides Encoding Cellulose Synthase and Fragments Thereof

The present invention relates to polynucleotides which comprise the nucleotide sequence that encodes cellulose synthase of the invention or a functional fragment thereof. In a suitable embodiment, the polynucleotide comprises the sequence encoding a tree cellulose synthase and most suitably, the sequence encoding a cellulose synthase from aspen. In one aspect, a polynucleotide of the invention includes the entire cellulose synthase coding region, e.g., nucleotides 69 to 3,005 of SEQ ID NO: 1. In another aspect of the invention, the polynucleotide encoding an *Arabidopsis* cellulose synthase is provided (see SEQ ID NO:4 and the translated protein of SEQ ID NO:5).

Also within the scope of the invention are fragments of the polynucleotides encoding cellulose synthase of the invention, which fragments encode at least one transmembrane domain and/or a UDP-glucose binding domain. For example, a polynucleotide comprising the nucleotides encoding a UDP-glucose binding domain of aspen cellulose synthase (e.g., nucleotides 660 to 2250 of SEQ ID NO:1) or corresponding nucleotides of SEQ ID NO:4 are within the scope of the invention. The nucleotides encoding the UDP-glucose binding domain can be determined by, for example, alignment of protein sequences as described below.

The invention further relates to sequence conservative variants of the coding portion of SEQ ID NOS. 1 and 4.

Polynucleotides that hybridize under conditions of low, medium, and high stringency to SEQ ID NOS: 1 and 4, and their respective coding portions are also within the scope of the invention. Preferably, the polynucleotide that hybridizes to any of SEQ ID NOS: 1 and 4, or their respective coding portions, is about the same length as that sequence, for example, not more than about 10 to about 20 nucleotides longer or shorter. In another embodiment of the invention, the hybridizable polynucleotide is at least 1500 nucleotides long, preferably at least 2500 nucleotides long and most preferably at least 3000 nucleotides long. In yet another embodiment, the hybridizable polynucleotide comprises the UDP-glucose binding domain as found in SEQ ID NO: 1 or 4, or at least the conserved region QVLRW [SEQ ID NO: 7]. Most preferably, the hybridizable polynucleotide has a UDP-glucose binding activity.

The polynucleotides that occur originally in nature may be isolated from the organisms that contain them using methods described herein or well known in the art. The non-naturally occurring polynucleotides may be prepared using various manipulations known in the field of recombinant DNA. For example, the cloned CelA polynucleotide can be modified according to methods described by Sambrook et al., 1989. The sequence can be cleaved at appropriate sites with restriction endonuclease(s), followed by further enzymatic modification if desired, isolated, and ligated in vitro. In the production of the modified polynucleotides, for example, care should be taken to ensure that the modified polynucleotide remains within the appropriate translational reading frame (if to be expressed) or uninterrupted by translational stop signals. As a further example, a CelA-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated CelA polynucleotide. Any technique for mutagenesis known in the art can be used, including but not limited to, in vitro site-directed mutagenesis Zoller and Smith, 1984, DNA 3:479–488; Oliphant et al., 1986, Gene 44:177; Hutchinson et al., 1986, Proc. Natl. Acad. Sci. U.S.A. 83:710), use of TAB linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The polynucleotides of the present invention may be introduced into various vectors adapted for plant or non-plant replication. These are well known in the art, thus, choice, construction and use of such vectors is well within the skill of a person skilled in the art. Possible vectors include, but are not limited to, plasmids or modified viruses of plants, but the vector system must be compatible with the host cell used. An example of a suitable vector is Ti plasmid. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. An expression cassette containing cellulose synthase or recombinant molecules thereof can be introduced into host cells via silicon carbide whiskers, transformed protoplasts, transformation, e.g., *Agrobacterium* vectors (discussed below), electroporation, infection, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2m plasmid.

Transgenic plants containing the polynucleotides described herein are also within the scope of the invention. Methods for introducing exogenous polynucleotides into plant cells and regenerating transgenic plants are well known. Some are provided below.

In one embodiment, to introduce a plasmid containing a CelA coding sequence or promoter of the invention into a plant, a 1:1 mixture of plasmid DNA containing a selectable marker expression cassette and plasmid DNA containing a cellulose synthase expression cassette is precipitated with gold to form microprojectiles. The microprojectiles are rinsed in absolute ethanol and aliquots are dried onto a suitable macrocarrier such as the macrocarrier available from BioRad in Hercules, Calif. Prior to bombardment, embryogenic tissue is preferably desiccated under a sterile laminar-flow hood. The desiccated tissue is transferred to semi-solid proliferation medium. The prepared microprojectiles are accelerated from the macrocarrier into the desiccated target cells using a suitable apparatus such as a BioRad PDS-1000/HE particle gun. In a preferred method, each plate is bombarded once, rotated 180 degrees, and bombarded a second time. Preferred bombardment parameters are 1350 psi rupture disc pressure, 6 mm distance from the rupture disc to macrocarrier (gap distance), 1 cm macrocarrier travel distance, and 10 cm distance from macrocarrier stopping screen to culture plate (microcarrier travel distance). Tissue is then transferred to semi-solid proliferation medium containing a selection agent, such as hygromycin B, for two days after bombardment.

Cellulose Synthase Protein and Fragment Thereof

A cellulose synthase of the invention is a plant protein that contains a catalytic subunit which has UDP-glucose binding activity for the synthesis of glucan from glucose, and eight transmembrane domains for localizing the cellulose synthase to the cell membrane. The cellulose synthase of the invention has eight transmembrane binding domains; two at the amino terminal and six at the carboxyl terminal. The UDP-glucose binding domain is located between transmembrane domains two and three. Examples of this protein structure are seen in the aspen cellulose synthase as well as in those of RSW1 and GhCelA. The location of the transmembrane domain may be identified as described below and as exemplified in the Example. Preferably, the cellulose synthase of the invention has an amino acid sequence of a tree cellulose synthase.

In one embodiment, the cellulose synthase protein of the invention is isolated from aspen. Aspen cellulose synthase contains about 978 amino acids and has a molecular weight of about 110 KDa and a pI of about 6.58. In one embodiment, the aspen cellulose synthase has the amino acid sequence of SEQ ID NO:2 as represented in FIG. 1. In another aspect, the invention relates to cellulose synthase of SEQ ID NO: 5.

The invention further relates to fragments of plant cellulose synthases, such as fragments containing at least one transmembrane region and/or a UDP-glucose binding domain. The transmembrane regions may be identified as described in the Example by using the method of Hoffman and Stoffel (1993).

The cellulose synthase fragment containing the UDP-glucose binding domain is functional without the presence of the rest of the protein. This separable activity is as shown in the Example. This result was surprising and unexpected because previously identified UDP-glucose binding domains were not known to be functional when isolated from other portions of the protein. Thus, a fragment of any cellulose synthase (such as PtCelA, RSW1, GhCelA and SEQ ID NO:5) that contains a UDP-glucose binding domain and is independently functional is within the scope of the invention. The function of the UDP-glucose binding domain may be determined using the assay described in the Example. The UDP-glucose binding domain of the invention is located between the second and third transmembrane region of the cellulose synthase and has conserved amino acid sequences for UDP-glucose binding, such as the sequence QVLRW and conserved D residues. The UDP-glucose binding domain and the conserved regions therein may be located in a cellulose synthase using the guidance of the present specification and the general knowledge in the art, for example Brown, 1996. In one embodiment, the UDP-glucose binding domain and the conserved regions therein may be identified by comparing the amino acid sequence of cellulose synthase of interest with the amino acid sequence of aspen cellulose synthase using the algorithms described in the specification or generally known in the art. For example, the UDP-glucose binding domain of SEQ ID NO:2 is in the position amino acids 220 to 749. The conserved QVLRW sequence is located at positions 715–719 of SEQ ID NO:2.

Polypeptides having at least 75%, preferably at least 85% and most preferably at least 95% similarity to the amino acid sequence of SEQ ID NO: 2, amino acids 220–749 of SEQ ID NO:2, SEQ ID NO:5 or its UDP-glucose binding domain using Power Blast or GAP algorithm described above. In a preferred embodiment, these polypeptides are of about the same length as the polypeptide of SEQ ID NO: 2 or amino acids 220–749 of SEQ ID NO:2. For example, the polypeptide may be from about 2–3 to about 5–7 and to about 10–15 amino acids longer or shorter. In another embodiment, the polypeptides described in this paragraph are not originally found (i.e., naturally occurring) in *Arabidopsis* or cotton. These polypeptides may be prepared by, for example, altering the nucleic acid sequence of a cloned polynucleotide encoding the protein of SEQ ID NO:2 or SEQ ID NO:5 using the methods well known in the art.

Function conservative variants of cellulose synthase are also within the scope of the invention and can be prepared by altering the sequence of a cloned polynucleotide encoding cellulose synthase or fragments thereof. Conventional methods used in the art can be used to make substitutions, additions or deletions in one or more amino acids, to provide functionally equivalent molecules. For example, a function conservative variant that has substitutions, deletions and/or additions in the amino and/or carboxyl terminus of the protein, outside of the UDP-glucose binding domain is within the scope of the invention. Preferably, variants are made that have enhanced or increased functional activity relative to native cellulose synthase. Methods of directed evolution can be used for this purpose.

The invention also includes function conservative variants which include altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point. Particularly preferred substitutions are: (i) Lys for Arg and vice versa such that a positive charge may be maintained; (ii) Glu for Asp and vice versa such that a negative charge may be maintained; (iii) Ser for Thr such that a free —OH can be maintained; and (iv) Gln for Asn such that a free $CONH_2$ can be maintained. Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces b-turns in the protein's structure.

The cellulose synthase of the invention can be isolated by expressing a cloned polynucleotide encoding the cellulose synthase as well as using direct protein purification techniques. These methods will be apparent to those of skill in the art.

Polynucleotides Containing Cellulose Synthase Promoter

The present invention further relates to a cellulose synthase promoter. The promoter is a stress-inducible promoter and may be used to synthesize greater quantities of high crystalline cellulose in plant, and preferably in trees. This permits an increase in the proportion of cellulose in transgenic plants, greater strength of juvenile wood and fiber, and acceleration of overall growth rate.

In one embodiment, the promoter of the invention is from aspen and is represented in FIG. 4. The promoter sequence is located within the region of nucleotides 1–840 of SEQ ID NO:3. A person of skill in the art will appreciate that not the entire sequence is required for the promoter function and can easily identify the critical regions by looking for conserves boxes and doing routine deletion analysis. Thus, functional fragments of SEQ ID NO:1 are within the scope of the invention.

Polynucleotides that hybridize under conditions of low, medium, and high stringency to SEQ ID NO:3, and its non-coding portion are also within the scope of the invention. The hybridizable polynucleotide may be about the same length as the sequence to which it hybridizes, for example, not more than about 10 to about 20 nucleotides longer or shorter. In another embodiment, the hybridizable polynucleotide is at least about 200 nucleotides long, preferably at least about 400 nucleotides long and most preferably at least 500 nucleotides long. In yet another embodiment, the hybridizable polynucleotide comprises at least one MSRE element identified according to the method described below.

A cellulose synthase promoter of the invention typically provides tissue-specific gene regulation in xylem, but also permits up-regulation of gene expression in other tissues as well, e.g., phloem under tension stress. Furthermore, expression of cellulose synthase is localized to an area of the plant under stress.

This stress-inducible phenomenon is regulated by positive and negative mechanical stress response elements (MSREs). These MSREs upregulate (positive) or downregulate (negative) the expression of a cellulose synthase polynucleotide under stress conditions through binding of transcription factors. MSRE-regulated expression of cellulose synthase permits synthesis of cellulose with high crystallinity.

The MSREs of cellulose synthase can be modified or employed otherwise in methods to regulate expression of a polynucleotide, including a cellulose synthase, operatively linked to a promoter containing an MSRE in response to mechanical stress (e.g., tension or compression) to a transgenic plant.

Negative MSREs of a cellulose synthase promoter can be modified, removed or blocked to improve expression of a cellulose synthase, and thereby increase cellulose production and improve wood quality. Alternatively, positive MSREs can be removed or blocked to decrease expression of a cellulose synthase, which decreases cellulose production and increases lignin deposition. This is useful for increasing the fuel value of wood because lignin has a higher BTU value than cellulose. Moreover, a modified cellulose synthase promoter can be operatively linked to a polynucleotide of interest to control its expression upon mechanical stress to a plant harboring it.

The location of MSRE elements in the SEQ ID NO:3 may be identified, for example, using promoter deletion analysis, DNAse Foot Print Analysis, and Southwestern screening of an expression library for an MSRE. In one embodiment, cellulose synthase promoter that has one or more portions deleted, and is operatively linked to a reporter sequence, is introduced into a plant or a plant cell. A positive MSRE is detected by observing no relative change or increase in the amount of reporter in a transgenic plant or tissue, e.g., phloem after inducing a stress to the plant, and a negative MSRE is detected by observing increases in the amount of reporter in the plant in the absence of any stress to the plant. A positive element is detected when by removing it, GUS expression goes down and by adding it kept at the same level or more. The negative element does not support, or suppress, expression of GUS and by removing it, normal or enhanced GUS expression is observed as compared to when negative element is present.

Manipulation of a MSRE binding sites and/or providing transcription factors that bind thereto, provides a mechanism to continuously produce high crystalline cellulose in woody plant cell walls of transgenic plants. For example, one having ordinary skill in the art can delete or block negative MSRE elements, or provide cDNA encoding protein(s) that bind the positive MSREs, to enable constitutive expression of a cellulose synthase without the requirement of a mechanical stress. The increased cellulose synthase, and therefore, increased cellulose content, can improve the strength properties of juvenile wood and fiber. It is also contemplated that the positive MSREs can be deleted or blocked, or cDNA in an antisense direction, which in the sense direction encodes a protein that binds a positive MSRE, can be provided, to reduce cellulose synthase activity and decrease cellulose production.

Method of Isolating Polynucleotides Encoding Cellulose Synthase

The invention further relates to identifying and isolating polynucleotides encoding cellulose synthase in plants, e.g., trees, (in addition to those polynucleotides provided in the Example and represented in FIG. 1 and FIG. 7). These polynucleotides may be used to manipulate expression of cellulose synthase with an objective to improve the cellulose content and properties of wood.

The method comprises identifying a nucleic acid fragment containing a sequence encoding cellulose synthase or a portion thereof by using a fragment of SEQ ID NOS:1 or 4 as a probe or a primer. Once identified, the nucleic acid fragment containing a sequence encoding cellulose synthase or a portion thereof is isolated.

Polynucleotides encoding cellulose synthases of the invention, whether genomic DNA, cDNA, or fragments thereof, can be isolated from many sources, particularly from cDNA or genomic libraries from plants, preferably trees (e.g. aspen, sweetgum, loblolly pine, eucalyptus, and other angiosperms and gymnosperms). Molecular biology methods for obtaining polynucleotides encoding a cellulose synthase are well known in the art, as described above (see, e.g., Sambrook et al., 1989, supra).

Accordingly, cells from any species of plant can potentially serve as a nucleic acid source for the molecular cloning of a polynucleotide encoding a cellulose synthase of the invention. The DNA may be obtained by standard procedures known in the art from cloned DNA (e.g., a DNA "library"), and preferably is obtained from a cDNA library prepared from tissues with high level expression of a cellulose synthase (e.g., xylem tissue, since cells in this tissue evidence very high levels of expression of CelA), by chemical synthesis, by cDNA cloning, or by the cloning of genomic DNA, or fragments thereof, purified from a desired cell (see, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, a polynucleotide should be molecularly cloned into a suitable vector for its propagation.

In another embodiment for the molecular cloning of a polynucleotide encoding a cellulose synthase of the invention from genomic DNA, DNA fragments are generated from a genome of interest, such as from a plant, or more particularly a tree genome, part of which will correspond to a desired polynucleotide. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing a desired CelA sequence may be accomplished in a number of ways. For example, if an amount of a portion of a CelA sequence or its specific RNA, or a fragment thereof, is available and can be purified and labeled, the generated DNA fragments may be screened by nucleic acid hybridization to a labeled probe (Benton and Davis, 1977, Science 196:180; Grunstein and Hogness, 1975, Proc. Natl. Acad. Sci. U.S.A. 72:3961). For example, a set of oligonucleotides corresponding to the partial amino acid sequence information obtained for a CelA protein from trees can be prepared and used as probes for DNA encoding cellulose synthase, or as primers for cDNA or mRNA (e.g., in combination with a poly-T primer for RT-PCR). Preferably, a fragment is selected that is highly unique to a cellulose synthase of the invention, such as the UDP-glucose binding regions. Those DNA fragments with substantial homology to the probe will hybridize. As noted above, the greater the degree of homology, the more stringent hybridization conditions can be used. In a specific embodiment, stringency hybridization conditions can be used to identify homologous CelA sequences from trees or other plants.

Thus, in one embodiment, a labeled cellulose synthase cDNA from, e.g. *Populus tremuloides* (PtCelA), can be used to probe a library of genes or DNA fragments from various species of plants, especially angiosperm and gymnosperm, to determine whether any bind to a CelA of the invention. Once genes or fragments are identified, they can be amplified using standard PCR techniques, cloned into a vector, e.g., pBluescript vector (StrataGene of LaJolla, Calif.), and transformed into a bacteria, e.g., DH5α *E. coli* strain (Gibco BRL of Gaithersburg, Md.). Bacterial colonies are typically tested to determine whether any contains a cellulose synthase-encoding nucleic acid. Once a positive clone is identified through binding, it is sequenced from an end, preferably the 3' end.

cDNA libraries can be constructed in various hosts, such as lambda ZAPII, available from Stratagene, LaJolla, Calif., using poly(A) +RNA isolated from aspen xylem, according to the methods described by Bugos et al. (Biotechniques 19:734–737, 1995). The above mentioned probes are used to assay the aspen cDNA library to locate cDNA which codes for enzymes involved in production of cellulose synthases. Once a cellulose synthase sequence is located, it is then cloned and sequenced according to known methods in the art.

Further selection can be carried out on the basis of the properties of the gene, e.g., if the gene encodes a protein product having the isoelectric, electrophoretic, hydropathy plot, amino acid composition, or partial amino acid sequence of a cellulose synthase protein of the invention, as described herein. Thus, the presence of the gene may be detected by assays based on the physical, chemical, or immunological properties of its expressed product. For example, cDNA clones or DNA clones which hybrid-select the proper mRNAs can be used to produce a protein that has similar properties known for cellulose synthases of the invention. Such properties may include, for example, similar or identical electrophoretic migration patterns, isoelectric focusing or non-equilibrium pH gel electrophoresis behavior, proteolytic digestion maps, hydropathy plots, or functional properties (such as isolated, functional UDP-glucose binding domains).

A cellulose synthase polynucleotide of the invention can also be identified by mRNA selection, i.e., by nucleic acid hybridization followed by in vitro translation. In this procedure, nucleotide fragments are used to isolate complementary mRNAs by hybridization. Such DNA fragments may represent available, purified CelA DNA, or may be synthetic oligonucleotides designed from the partial amino acid sequence information. Functional assays (e.g., UDP-glucose activity) of the in vitro translation products of the products of the isolated mRNAs identifies the mRNA and, therefore, the complementary DNA fragments, that contain the desired sequences.

A radiolabeled CelA cDNA can be synthesized using a selected mRNA as a template. The radiolabeled mRNA or cDNA may then be used as a probe to identify homologous CelA DNA fragments from amongst other genomic DNA fragments.

It will be appreciated that other polynucleotides, in addition to a CelA of the invention can be operatively linked to a CelA promoter to control expression of the polynucleotide upon application of a mechanical stress.

Expression of CelA Polypeptides

The nucleotide sequence coding for CelA, or a functional fragment, derivative or analog thereof, including chimeric proteins, can be inserted into an appropriate expression vector, i.e., a vector which contains the necessary elements for the transcription and translation of the inserted protein-coding sequence. Preferably, an expression vector includes an origin of replication. The elements are collectively termed herein a "promoter." Thus, a nucleic acid encoding CelA of the invention can be operatively associated with a promoter in an expression vector of the invention. Both cDNA and genomic sequences can be cloned and expressed under control of such regulatory sequences. The necessary transcriptional and translational signals can be provided on a recombinant expression vector, or they may be supplied by the native gene encoding CelA and/or its flanking regions.

In addition to a CelAP, expression of cellulose synthase can be controlled by any promoter/enhancer element known in the art, but these regulatory elements must be functional in the host selected for expression. Promoters which may be used to control CelA polynucleotide expression include, constitutive, development-specific and tissue-specific. Examples of these promoters include 35S Cauliflower Mosaic Virus, terminal flower and 4CL-1. Thus, there are various ways to alter the growth of a plant using different promoters, depending on the needs of the practitioner.

The nucleotide sequence may be inserted in a sense or antisense direction depending on the needs of the practitioner. For example, if augmentation of cellulose biosynthesis is desired then polynucleotides encoding, e.g., cellulose synthase, can be inserted into the expression vector in the sense direction to increase cellulose synthase production and thus cellulose biosynthesis. Alternatively, if it is desired that cellulose biosynthesis is reduced or lignin content is increased, then polynucleotides encoding, e.g., cellulose synthase, can be inserted in the antisense direction so that upon transcription the antisense mRNA hybridizes to other complementary transcripts in the sense orientation to prevent translation. In other embodiments, the polynucleotide encodes a UDP-glucose binding domain and is used in a similar manner as described.

A recombinant CelA protein of the invention, or functional fragment, derivative, chimeric construct, or analog thereof, may be expressed chromosomally, after integration of the coding sequence by recombination. In this regard, any of a number of amplification systems for plants may be used to achieve high levels of stable gene expression, as discussed above. Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression vectors containing a nucleic acid encoding a CelA of the invention can be identified by four general approaches: (a) PCR amplification of the desired plasmid DNA or specific mRNA, (b) nucleic acid hybridization, (c) presence or absence of selection marker gene functions, (d) analyses with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-glucuronidase activity, resistance to antibiotics, transformation phenotype, etc.) caused by the insertion of foreign genes in the vector. In another example, if the nucleic acid encoding CelA is inserted within the "selection marker" gene sequence of the vector, recombinants containing the CelA insert can be identified by the absence of the CelA gene function. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, provided that the expressed protein assumes a functionally active conformation.

After a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to those vectors or their derivatives described above.

Vectors are introduced into the desired host cells by methods known in the art, e.g., *Agrobacterium*-mediated transformation (described in greater detail below), transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967: Wu and Wu, 1988, J. Biol. Chem. 263: 14621–14624; Hartmut et al., Canadian Patent Application No. 2,012,311, filed Mar. 15, 1990).

The cell into which the recombinant vector comprising the nucleic acid encoding CelA is cultured in an appropriate cell culture medium under conditions that provide for expression of CelA by the cell. In addition, a host cell strain may be chosen which modulates the expression of the inserted sequences, or modifies and processes the gene product in a specific fashion desired. Different host cells have characteristic and specific mechanisms for the translational and post-translational processing and modification (such as glycosylation, cleavage, e.g., of a signal sequence) of proteins. Appropriate cell lines or host systems can be chosen to ensure the desired modification and processing of the foreign protein expressed.

*Agrobacterium*-Mediated Transformation and Inducing Somatic Embryos

The culture media used in the invention, and for transforming *Agrobacterium*, contain an effective amount of each of the medium components (e.g. basal medium, growth regulator, carbon source) described above. As used in describing the present invention, an "effective amount" of a given medium component is the amount necessary to cause a recited effect. For example, an effective amount of a growth hormone in the primary callus growth medium is the amount of the growth hormone that induces callus formation when combined with other medium components. Other compounds known to be useful for tissue culture media, such as vitamins and gelling agents, may also be used as optional components of the culture media of the invention.

Transformation of cells from plants, e.g., trees, and the subsequent production of transgenic plants using *Agrobacterium*-mediated transformation procedures known in the art, and further described herein, is one example of a method for introducing a foreign gene into trees. Transgenic plants may be produced by various methods, such as by the following steps: (i) culturing *Agrobacterium* in low-pH induction medium at low temperature and preconditioning, i.e., coculturing bacteria with wounded tobacco leaf extract in order to induce a high level of expression of the *Agrobacterium vir* genes whose products are involved in the T-DNA transfer; (ii) coculturing a desired plant tissue explants, including zygotic and/or somatic embryo tissues derived from cultured explants, with the incited *Agrobacterium*; (iii) selecting transformed callus tissue on a medium containing antibiotics; and (v) and converting the embryos into plantlets.

Any non-tumorigenic *A. tumefaciens* strain harboring a disarmed Ti plasmid may be used in the method of the invention. Any *Agrobacterium* system may be used. For example, Ti plasmid/binary vector system or a cointegrative vector system with one Ti plasmid may be used. Also, any marker gene or polynucleotide conferring the ability to select transformed cells, callus, embryos or plants and any other gene, such as, for example, a gene conferring resistance to a disease, or one improving cellulose content, may also be used. Any promoter desired can be used, such as, for example, a PtCelAP of the invention, and those promoters as described above. A person of ordinary skill in the art can determine which markers and genes are used depending on particular needs.

For purposes of the present invention, "transformed" or "transgenic" means that at least one marker gene or polynucleotide conferring selectable marker properties is introduced into the DNA of a plant cell, callus, embryo or plant. Additionally, any gene may also be introduced.

To increase the infectivity of the bacteria, *Agrobacterium* is cultured in low-pH induction medium, i.e., any bacterium culture media with a pH value adjusted to from 4.5 to 6.0, most preferably about 5.2, and at low temperature such as for example about 19–30° C., preferably about 21–26° C. The conditions of low-pH and low temperature are among the well-defined critical factors for inducing virulence activity in *Agrobacterium* (e.g., Altmorbe et al., Mol. Plant-Microbe. Interac. 2: 301, 1989; Fullner et al., Science 273: 1107, 1996; Fullner and Nester, J. Bacteriol. 178: 1498, 1996).

The bacteria is preconditioned by coculturing with wounded tobacco leaf extract (prepared according to methods known generally known in the art) to induce a high level of expression of the *Agrobacterium vir* genes. Prior to inoculation of plant somatic embryos, *Agrobacterium* cells can be treated with a tobacco extract prepared from wounded leaf tissues of tobacco plants grown in vitro. To achieve optimal stimulation of the expression of *Agrobacterium vir* genes by wound-induced metabolites and other cellular factors, tobacco leaves can be wounded and precultured overnight. Culturing of bacteria in low pH medium and at low temperature can be used to further enhance the bacteria vir gene expression and infectivity. Preconditioning with tobacco extract and the vir genes involved in the T-DNA transfer process are generally known in the art.

*Agrobacterium* treated as described above is then cocultured with a plant tissue explant, such as for example zygotic and/or somatic embryo tissue. Non-zygotic (i.e., somatic) or zygotic tissues can be used. Any plant tissue may be used as a source of explants. For example, cotyledons from seeds, young leaf tissue, root tissues, parts of stems including nodal explants, and tissues from primary somatic embryos such as the root axis may be used. Generally, young tissues are a preferred source of explants.

The invention also relates to methods of altering the growth of a plant by expressing the polynucleotide of the invention, which as a result alters the growth of the plant. The polynucleotide used in the method may be a homologous polynucleotide or a heterologous polynucleotide and are described in detail above. For example, both full-length and UDP-glucose binding region containing fragments may be expressed. Additionally, depending on the aim of the method, the polynucleotide may be introduced into the plant in the sense or in the antisense orientation. Any suitable promoter may be used to provide expression. The promoter or a functional fragment thereof is operatively linked to the polynucleotide. The promoter may be a constitutive promoter, a tissue-specific promoter or a development-specific plant promoter. Examples of suitable promoters are Cauliflower Mosaic Virus 35S, 4CL, cellulose synthase promoter, PtCelAP and terminal flower promoter.

The invention further relates to a method of altering the cellulose content in a plant by expressing the polynucleotide of the invention as described above. The method may be used to increased the ratio of cellulose to lignin in the plant that have an exogenous polynucleotide of the invention introduced therein.

The invention further relates to a method for altering expression of a cellulose synthase in a plant cell by introducing into the cell a vector comprising a polynucleotide of the invention and expressing the polynucleotide. The polynucleotides and promoters described above may be used.

A method for causing stress-induced gene expression in a plant cell is also within the scope of the invention. The method comprises (i) introducing into the plant or a plant cell an expression cassette comprising a cellulose synthase promoter or a functional fragment thereof or providing a plant or a plant cell that comprises the expression cassette (The promoter of the cassette is operatively linked to a coding sequence of choice.); and (ii) applying mechanical stress to the plant to induce expression of the desired coding sequence.

A method for determining a positive mechanical stress responsive element (MSRE) in a cellulose synthase promoter is also within the scope of the invention and comprises (i) making serial deletions in the cellulose synthase promoter, such as for example, SEQ ID NO:3; (ii) introducing the deletion linked to a polynucleotide encoding a reporter sequence into a plant cell, and (iii) detecting a decrease in the amount of reporter in the plant after inducing a stress to the plant. Similarly, a method for determining a negative MSRE in a cellulose synthase promoter is provided. It comprises (i) making serial deletions in the cellulose synthase promoter, such as for example, SEQ ID NO:3; (ii) introducing the deletion linked to a polynucleotide encoding a reporter sequence into a plant cell, and (iii) detecting an increase in the amount of reporter in the plant after inducing a stress to the plant.

The following methods are also within the scope of the invention: a method for expressing cellulose synthase in a tissue-specific manner comprising transforming a plant with a tissue specific promoter operatively linked to a polynucleotide encoding a cellulose synthase; a method for inducing expression of a cellulose synthase in a plant comprising introducing into a plant a cDNA encoding a protein that binds to a positive MSRE of a cellulose synthase promoter, thereby resulting in increased expression of cellulose in the plant, wherein the binding to the positive MSRE results in expression of a cellulose synthase; a method for reducing expression of a cellulose synthase comprising introducing into a plant a cDNA in an antisense orientation, wherein the cDNA in a sense orientation encodes a protein that binds to a positive MSRE and results in expression of a cellulose synthase; a method for increasing cellulose biosynthesis in a plant comprising introducing into a plant a cDNA encoding a protein that binds to a positive MSRE of a cellulose synthase promoter, whereby binding of the protein to the positive MSRE results in expression of a cellulose synthase, and A method for reducing cellulose biosynthesis in a plant comprising introducing into a plant a cDNA in an antisense orientation, wherein the cDNA in a sense orientation encodes a protein that binds to a positive MSRE of a cellulose synthase promoter.

EXAMPLE

Molecular Cloning of Cellulose Synthase

This Example describes the first tree cellulose synthase cDNA (PtCelA, GenBank No. AF072131) cloned from developing secondary xylem of aspen trees using RSW1 cDNA.

Prior to the present invention, only partial clones of cellulose synthases from crop species and cotton GhCelA have been discovered, which have significant homology to each other. The present inventors have discovered and cloned a new full-length cellulose synthase cDNA, AraxCelA (GenBank No. AF062485) (FIG. 7, [SEQ ID NO: 4]), from an *Arabidopsis* primary library. AraxCelA is a new member of cellulose synthase and shows 63–85% identity and 72–90% similarity in amino acid sequence with other *Arabidopsis* CelA members.

Another cellulose synthase was cloned in aspen using a $^{32}$P-labeled 1651-bp long EcoRI fragment of *Arabidopsis* CelA cDNA, which encodes a centrally located UDP-glucose binding domain, was used as a probe to screen about 500,000 pfu of a developing xylem cDNA library from aspen (*Populus tremuloides*) (Ge and Chiang, 1996). Four positive clones were obtained after three rounds of plaque purification. Sequencing the 3' ends of these four cDNAs showed that they were identical clones. The longest cDNA clone was fully sequenced and determined to be a full-length cDNA having a 3232 bp nucleotide sequence (FIG. 1) [SEQ ID NO: 1], which encodes a protein of 978 amino acids [SEQ ID NO: 2].

Characterization of a Cellulose Synthase from Aspen

The first AUG codon of PtCelA was in the optimum context for initiation of transcription on the basis of optimal context sequence described by Joshi (1987a) and Joshi et al. (1997). A putative polyadenylation signal (AATACA) was found 16 bp upstream of a polyadenylated tail of 28 bp, which is similar to the proposed plant structure (Joshi, 1987b). The 5' untranslated leader was determined to have 68 bp and the 3' untranslated trailor was 227 bp. Both of these regions have a typical length observed in many plant genes (Joshi, 1987a and Joshi, 1987b). This cDNA clone exhibited 90% amino acid sequence similarity with cellulose synthase from cotton (GhCelA,) and 71% with cellulose synthase from *Arabidopsis* (RSW1), suggesting that this particular tree homolog also encodes a cellulose synthase.

The full-length cDNA was designated PtCelA, and encodes a 110,278 Da polypeptide having an isoelectric point (pI) of 6.58 and 8 charged molecules. The hydropathy curve indicated that this particular cellulose synthase has eight transmembrane binding domains; two at the amino terminal and six at the carboxyl terminal, using the method of Hoffman and Stoffel (1993). This protein structure is analogous to those of RSW1 and GhCelA. All of the conserved domains for UDP-glucose binding, such as QVLRW and conserved D residues, are also present in a cellulose synthase of the invention, e.g., PtCelA (Brown et al., 1996). Thus, based on sequence and molecular analyses, it was concluded that PtCelA encodes a catalytic subunit which, like RSW1 in *Arabidopsis*, is essential for the cellulose biosynthesis machinery in aspen.

In situ localization of PtCelA mRNA transcripts along the developmental gradient defined by stem primary and secondary growth demonstrated that cellulose synthase expression is confined exclusively to developing xylem cells undergoing secondary wall thickening. This cell-type-specific nature of PtCelA gene expression was also consistent with xylem-specific activity of cellulose synthase promoter (PtCelAP) based on heterologous promoter-β-glucuronidase (GUS) fusion analysis. Overall, the results provide several lines of evidence that cellulose synthase is the gene primarily responsible for cellulose biosynthesis during secondary wall formation in woody xylem of trees, such as aspen. Previous results by the inventors (Hu et al., 1999) showed that cellulose and lignin are deposited in a compensatory fashion in wood. The discovery of a cellulose synthase in trees, such as aspen, permits the up-regulation of the protein to elevate cellulose production. Surprisingly, expression of CelA in trees suppressed lignin biosynthesis to further improve wood properties of trees.

Preparation of Transgenic Plants

The UDP-glucose binding sequence was subcloned into pBI121, which was used to prepare transgenic tobacco plants (Hu et al., 1998). The expression of a heterologous UDP-glucose binding sequence resulted in a remarkable growth-accelerating effect. This was surprising because current knowledge of the function of plant cellulose synthases teaches that a UDP-glucose sequence must remain intact with other functional domains in CelA, e.g., the transmembrane domains, in order for cellulose synthase to initiate cellulose biosynthesis. The remarkable growth and tremendous increase in plant biomass observed in transgenic tobacco was due likely to an augmented deposition of cellulose, indicating that the UDP-glucose domain alone is sufficient for genetic augmentation of cellulose biosynthesis in plants.

Genome Organization and Expression of a Novel Cellulose Synthase

To confirm that the cDNA clone of FIG. 1 [SEQ ID NO: 1] was a cellulose synthase, genomic Southern blot analysis was performed under both high and low stringency conditions using the cDNA. Genomic DNA from aspen was digested with PstI (lane P), HindIII (lane H) and EcoRI (lane E), and probed using a 1 kb $^{32}$P-labeled fragment from the 5' end of a cellulose synthase of FIG. 1. The Southern blot suggested the presence of a small family of cellulose synthase genes in aspen genome (FIG. 2, panels a and b). Repeated screening of the aspen xylem cDNA library with various plant CelA gene-related probes always resulted in the isolation of the same cellulose synthase cDNA clone. This suggested that the cellulose synthase cDNA cloned (FIG. 1) [SEQ ID NO: 1], represents the primary and most abundant cellulose synthase-encoding gene in developing xylem of trees, such as aspen, where active cellulose deposition takes place. It also indicates that manipulation of cellulose synthase gene expression can have a profound influence on cellulose biosynthesis in trees.

In Situ Hybridization

Northern blot analysis of total RNA from the internodes of aspen seedling stems (FIG. 2, panel c) using the labeled probe (as described above) revealed the near absence of cellulose synthase transcripts in tissues undergoing primary growth (internodes 1 to 4), and that the presence of cellulose synthase transcripts occurs during the secondary growth of stem tissues (internodes 5 to 11). However, weak northern signals in primary growth may only suggest that cellulose synthase gene expression is specific to xylem, of which there is little in primary growth tissue.

Xylogenesis in higher plants offers a unique model that involves sequential execution of cambium cell division, commitment to xylem cell differentiation, and culmination in xylem cell death (Fukuda, 1996). Although primary and secondary xylem cells originate from different types of cambia, namely procambium and inter/intrafascicular cambium, both exhibit conspicuous secondary wall development with massive cellulose and lignin deposition (Easu, K., 1960, Anatomy of Seed Plants, N.Y.: John Wiley and Sons). To further investigate spatial and temporal cellulose synthase gene expression patterns at the cellular level, in situ hybridization was used to localize cellulose synthase mRNA along the developmental gradient defined by stem primary and secondary growth.

Localization of cellulose synthase gene transcripts (RNA) in stem at various growth stages was also observed. FIG. 3 shows transverse sections from $2^{nd}$, 4th and $6^{th}$ internodes hybridized with digoxygenin (DIG)-labeled cellulose synthase antisense or sense (control) RNA probes, as described.

PtCelA transcripts were detected in young aspen stem sections by in situ hybridization with transcripts of highly variable 5' region of PtCelA cDNA (a 771 bp long fragment generated from PstI and SacI). This region was first subcloned in the plasmid vector, pGEM, -3Zf (+) (Promega) for the production of digoxygenin (DIG)-labeled transcripts using T7 (for antisense transcripts) and SP6 (for sense transcripts) RNA polymerase (DIG system: Boehringer Mannheim). Probes were subjected to mild alkaline hydrolysis by incubation in 100 mM $NaHCO_3$, pH 10.2 at 60° C., which produced approximately 200 bp fragments.

Aspen young stems were prepared for sectioning by fixation in 4% (w/v) paraformaldehyde in 100 mM phosphate buffer (pH 7.0) at 4° C. overnight, dehydrated through an ethanol series on ice, and embedded in Paraplast medium (Sigma). Ten µm sections were mounted on Superfrost/plus (Fisher) slides at 42° C. overnight, dewaxed and then rehydrated through a descending ethanol series. The sections were incubated with proteinase K (10 µg/ml in 100 mM Tris-HCl, 50 mM EDTA, pH 7.5) for 30 min and were post-fixed with FAA. The sections were acetylated with 0.33% (v/v) acetic anhydride in 0.1 M triethanolamine-HCl (pH 8.0) prior to hybridization. The sections were then incubated in a hybridization mixture (approximately 2 µg/ml DIG-labeled probes, 50% (v/v) formamide, 2× SSPE, 10% (w/v) dextran sulfate, 125 µg/ml tRNA, pH 7.5) at 45° C. for 12–16 hrs. Nonhybridized single-stranded RNA probe was removed by treatment with 20 µg/ml RNase A in TE buffer with 500 mM NaCl. The sections were washed at 50° C. Hybridized DIG-labelled probe was detected on sections using anti-digoxygenin antiserum at a 1:1500 dilution, as described in the manufacturer's instruction (DIG system: Boehringer Mannheim). Sections were examined by Eclipse 400 light microscope (Nikon) and photographed.

During the primary growth stage (FIG. 3, panels a and b), strong expression of cellulose synthase was found localized exclusively to primary xylem (PX) cells. At this stage, young internodes are elongating, resulting in thickening of primary xylem cells through formation of secondary walls (Easu, K., 1960, Anatomy of Seed Plants, New York: John Wiley and Sons). The concurrence of shoot elongation with high expression of cellulose synthase strongly suggests the association of cellulose synthase protein with secondary cell wall cellulose synthesis. Later stages of primary growth (FIG. 3, panel b) are characterized by the appearance of an orderly alignment of primary xylem cells. Active cellulose biosynthesis accompanies cell elongation-induced wall thickening, as indicated by the strong expression of cellulose synthase in these primary xylem cells.

At the beginning of secondary growth in older internodes, it was observed that expression of cellulose synthase is also exclusively localized to xylem cells (FIG. 3, panel c). Instead of elongation in internodes distal to the meristematic activity, growth at this stage is mainly radial due to thickening in secondary cell walls of secondary xylem. At the same time, expression of PtCelA gene becomes localized to the secondary developing xylem cells (SX in FIG. 3, panel c), which is again consistent with the idea that PtCelA encodes a secondary cell wall cellulose synthase. At this stage, secondary xylem cells cover the elongated and differentiated primary xylem cells in which PtCelA gene expression is no longer detectable (FIG. 3, panel c). These results demonstrate that expression of PtCelA gene is xylem-specific and the cellulose synthase of FIG. 1 [SEQ ID NO: 1] encodes a cellulose synthase associated with cellulose biosynthesis in secondary walls of xylem cells. To further confirm xylem-specific expression of cellulose synthase, a cellulose synthase gene promoter sequence was cloned and characterized for regulatory activities.

Characterization of Expression Regulated by Cellulose Synthase Promoter

A 5' 1,200 bp cDNA fragment of a cellulose synthase of FIG. 1 [SEQ ID NO: 1] was used as a probe to screen an aspen genomic library for 5' regulatory sequences of a novel cellulose synthase gene, PtCelA. The library was constructed by cloning aspen genomic DNA fragments, generated from an Sau3AI partial-digest and sucrose gradient-selected, into the BamHI site of a Lambda DASH II vector (Stratagene, La Jolla, Calif.). Five positive clones were obtained from about 150,000 pfu and Lambda DNA was purified. One clone having about a 20 kb DNA insert size was selected for restriction mapping and partial sequencing. This resulted in the identification of a 5' flanking region of PtCelA gene of approximately 1 kb. This genomic fragment, designated PtCelAP (FIG. 4) [SEQ ID NO: 3], contained about 800 bp of promoter sequence, 68 bp of 5' end untranslated region and 160 bp of coding sequence. To investigate regulation of tissue-specific cellulose synthase expression at the cellular level, promoter activity was analyzed in transgenic tobacco plants by histochemical staining of a GUS protein. A PtCelAP-GUS fusion binary vector was constructed in pBI121 with the 35S promoter replaced with PtCelAP [SEQ ID NO: 3] and introduced into tobacco (*Nicotiana tabacum*) as per Hu et al. (1998).

Eleven independent transgenic lines harboring a CelAP-GUS fusion were generated. FIG. 5 shows a histochemical analysis of GUS expression driven by a cellulose synthase promoter of the invention in transgenic tobacco plants. Transverse sections from the 3rd (panel a), 5th (panel b), 7th (panel c), and 8th (panels d and f) internodes were stained from GUS activity, and fluorescence microscopy was used to visualize expression under UV radiation.

GUS staining was detected exclusively in xylem tissue of stems, roots and petioles. In stems, strong GUS activity was found localized to xylem cells undergoing primary (FIG. 5, panel a) and secondary growth (FIG. 5 panels b–d and f). GUS expression was confined to xylem cells in the primary growth stage and became more localized in developing secondary xylem cells during secondary growth. An entire section from the 8th internode stained for GUS activity (FIG. 5, panel f) These results are consistent with the in vivo expression patterns of cellulose synthase in aspen stems. Lignin autofluorescence was visualized after UV radiation. Phloem fibers, which are also active in cellulose and lignin biosynthesis (FIG. 5, panels d and e), did not show GUS activity, suggesting that cellulose synthase gene expression is not associated with cellulose biosynthesis in cell types other than xylem. Examination of GUS activity in roots, stems, leaves, anthers and fruit also showed GUS expression in xylem tissue of all these organs suggesting that cellulose synthases of the invention are xylem-specific cellulose and expressed in all plant organs.

Characterization of promoter activity and cellular expression of a cellulose synthase of the invention from one particular source (aspen) indicated that expression produces a protein that encodes a secondary cell wall-specific cellulose synthase and is specifically compartmentalized in developing xylem cells. Characterization of the cellulose synthase gene promoter sequence not only confirms cell type-specific expression of cellulose synthase, but also provides a method for over-expressing cellulose synthase in a tissue-specific manner to augment cellulose production in xylem.

Expression of Cellulose Synthase Under Tension Stress

As described earlier, a cellulose synthase promoter of the invention is involved in a novel gene regulatory phenomenon of cellulose synthase. To further characterize a cellulose synthase of the invention, GUS expression driven by an aspen cellulose synthase promoter (PtCelAP) was observed in transgenic tobacco plants without or under tension stress. The stress was induced by bending and affixing the plants to maintain the bent position (e.g., tying) over a 40 hour period. Tangential and longitudinal sections were taken before bending, and 4 hrs, 20 hrs and 40 hrs after bending (panels a–d, respectively).

The cellulose synthase promoter-GUS fusion binary constructs showed exclusive xylem-specific expression of GUS without any tension stress (FIG. 6, panel a). However, under tension stress conditions endured by angiosperms in nature, the transgenic tobacco plants induced xylem and phloem-specific expression on the upper side of the stem within the first four hours of stress (FIG. 6, panel b).

This observation was surprising because during tension wood development fibers produce highly crystalline cellulose in order to provide essential mechanical strength to a bending stem. The present observation was the first showing of transcriptional up-regulation of a cellulose synthase, mediated through a cellulose synthase promoter that is directly responsible for development of highly crystalline cellulose in trees. Furthermore, after 20 hrs of tension stress, both xylem and phloem exhibited GUS expression, but only on the upper side of the stem that was under tensile stress, i.e., GUS expression on the lower side was inhibited (FIG. 6, panel c). With extended stress (up to 40 hrs), GUS expression was restricted to only one small region on the upper side of the stem where maximum tension stress was present (FIG. 6, panel d). Based on the observation of GUS signal in woody cells upon tension stress and the absence of GUS under compression or no stress, it was concluded that a cellulose synthase promoter of the invention has mechanical stress responsive elements (MSREs) that turn cellulose synthase genes on and off depending on the presence and type of stress to the stem.

The results indicate that positive MSREs exist in a cellulose synthase promoter of the invention to bind transcription factors in response to tension stress for regulating the expression of cellulose synthase and increasing biosynthesis of higher crystalline cellulose. This is evident based on the expression of GUS in xylem and phloem tissue at the upper side of the stem subjected to tension stress, but not when tissue on the lower side was subjected to compression or no stress. Furthermore, the tissue at the lower side of the stem, which was subjected to compression stress, showed no GUS expression, i.e., expression was turned off. This indicated the presence of negative MSREs, which bind transcription factors to turn off expression of cellulose synthase at the lower side of the stem. Negative MSREs likely suppress development of highly crystalline cellulose in normal wood.

These results provide a mechanism for genetically engineering synthesis of highly crystalline cellulose in juvenile wood for enhancing strength properties, and for synthesizing a higher percentage of cellulose in reaction wood. The positive MSREs and their cognate transcription factors are important in the synthesis of highly crystalline cellulose of high tensile strength, as are the negative MSREs and inhibition of cognate transcription factors thereto. The present invention thus provides a starting point for cloning cDNAs for the transcription factors that bind to positive and negative MSREs according to methods known in the art. Constitutive expression of cDNAs for positive MSRE transcription factors allows the continuous production of highly crystalline cellulose in transgenic trees, while expression of antisense cDNAs for negative MSRE transcription factors inhibits those transcription factors so that cellulose synthase cannot turn off. This combination will assure continuous production of highly crystalline cellulose in trees.

Genetic Engineering of Cellulose Synthase in Transgenic Plants

As discussed above, the nucleotide sequence of a cellulose synthase of the invention, e.g., PtCelA cDNA from aspen, shows significant homology with other polynucleotides encoding cellulose synthase proteins that have been suggested as authentic cellulose synthase clones. To further characterize the activity of a cellulose synthase, four constructs were prepared in a PBI121 plasmid.

1) A constitutive plant promoter Cauliflower mosaic Virus 35S was operatively linked to PtCelA (35SP-PtCelA-s) and overexpressed in transgenic plants. This causes excess production of cellulose, resulting in a reduction in lignin content. Tobacco and aspen have been transformed with this construct.

2) Cauliflower mosaic Virus 35S was operatively linked to antisense RNA from PtCelA (35S-PtCelA-a) and constitutively expressed to reduce production of cellulose and increase lignin content in transgenic plants. This negative control construct may not result in healthy plants since cellulose is essential for plant growth and development. Aspen plants have been transformed with this construct.

3) Aspen 4CL-1 promoter (Hu et al., 1998) was operatively linked to PtCelA (Pt4CLP-PtCelA) (the 35S promoter of PBI121 was removed in this construct) and expressed in a tissue-specific manner in developing secondary xylem of transgenic aspen. This expression augments the native cellulose production and reduces lignin content of angiosperm tissues. Tobacco and aspen have transformed with this construct.

4) The cytoplasmic domain of PtCelA which contains three conserved regions thought to be involved in UDP-glucose binding during cellulose biosynthesis, was linked to a 35S promoter to produce binary constructs (35S-PtCelA UDP-glucose). Expression by this promoter permits constitutive expression of a UDP glucose binding domain of PtCelA in transgenic plants. Tobacco and aspen have been transformed with this construct.

35S-GUS constructs (pBI121, ClonTech, CA) were used as controls for each experiment with the constructs. Transgenic tobacco plants were transformed with the constructs. The following table shows the general growth measurements of the T0 tobacco plants. Plants carrying a PtCelA construct grew much faster than control plants carrying a pBI121 (control) construct. In comparing developmental 4CL and constitutive 35S promoter control of PtCelA expression, the 35S was more effective, permitting faster growth of transgenic tobacco plants. The fastest growth was seen in transgenic plants carrying a 35S promoter driven UDP-G domain from PtCelA.

It is noted that T0 generation plants can have carry over effects from their tissue culture treatments. Therefore, seeds were collected for testing this growth phenomenon in T1 generations. The transgenic tobacco plants were analyzed for presence of the transferred genes and all tested positive for the respective gene constructs.

TABLE

Transgenic tobacco plant measurements
after transfer in soil for about 1.5 months (N = 2)

| Construct | Height | Diameter | Internode length | No. of leaves | Longest leaf |
|---|---|---|---|---|---|
| 35S-GUS | 17 | 0.5 | 1 | 11 | 17 |
| 35S-PtCelA | 77 | 1.0 | 6 | 13 | 37 |
| 35S-UDPG | 83 | 1.0 | 6 | 13 | 37 |
| 4CLP-PtCelA | 41 | 0.8 | 5 | 10 | 29 |

Note: All values were measured in centimeters, excluding number of leaves.

It will be appreciated by persons of ordinary skill in the art that the examples and preferred embodiments herein are illustrative, and that the invention may be practiced in a variety of embodiments which share the same inventive concept.

BIBLIOGRAPHY

Hu et al., 1999, Nature Biotechnology. In Press
Whetten et al., 1998, Ann Rev Pl Physiol Pl Mol Biol, 49: 585–609
Arioli et al., 1998, Science, 279: 717–720
Wu et al., 1998, Pl Physiol, 117: 1125
Hu et al., 1998, PNAS, 95: 5407–5412
Joshi et al., 1997, PMB, 35: 993–1001
Fukuda, 1996, Ann Rev Pl Physiol Pl Mol Biol, 47: 299–325
Pear et al., 1996, PNAS, 93: 12637–12642
Haigler and Blanton, 1996, PNAS, 93: 12082–12085
Ge and Chiang, 1996, Pl Physiol, 112: 861
Brown et al., 1996, Trends Pl Sci., 1: 149–156
Delmer and Amor, 1995, Pl Cell, 7: 987–1000
Hoffman and Stoffel, 1993, Biol Chem, Hoppe-Seyler 374: 166
Joshi, 1987, NAR, 15: 6643–6653
Joshi, 1987, NAR, 15: 9627–9640
Timmell, 1986, Compression Wood in Gymnopserms, Springer Verlag
Easu, K., 1960. Anatomy of Seed Plants, New York: John Wiley and Sons
Higuchi, 1997, Biochemistry and Molecular Biology of Wood, Springer Verlag

What is claimed is:

1. An isolated polynucleotide encoding a polypeptide comprising the amino acid sequence from position 220 to position 749 of SEQ ID NO: 2, wherein the polypeptide has cellulose synthase activity.

2. The polynucleotide of claim 1, wherein the polypeptide comprises SEQ ID NO: 2.

3. The polynucleotide of claim 1, wherein the polynucleotide comprises the nucleotide sequence from position 660 to position 2250 of SEQ ID NO: 1.

4. A transgenic plant cell comprising an exogenous polynucleotide encoding a polypeptide comprising the amino acid sequence from position 220 to position 749 of SEQ ID NO: 2, wherein the polypeptide has cellulose synthase activity.

5. A transgenic plant comprising the plant cell of claim 4.

6. The transgenic plant of claim 5, wherein the plant is a tree.

7. A vector comprising an isolated polynucleotide encoding a polypeptide comprising the amino acid sequence from position 220 to position 749 of SEQ ID NO: 2, wherein the polypeptide has cellulose synthase activity and wherein the polynucleotide is operably linked with a promoter sequence functional in a plant.

8. A transgenic plant cell comprising the vector of claim 7.

9. A method for producing a transgenic plant cell comprising introducing into the plant cell an exogenous polynucleotide encoding a polypeptide comprising the amino acid sequence from position 220 to position 749 of SEQ ID NO: 2, wherein the polypeptide has cellulose synthase activity.

10. The method of claim 9, wherein the polynucleotide is operably associated with a promoter.

11. The method of claim 9, wherein the polynucleotide comprises nucleotides from position 660 to position 2250 of SEQ ID NO: 1.

12. The method of claim 9, wherein the polynucleotide comprises the nucleotide sequence from position 69 to position 3005 of SEQ ID NO: 1.

13. The method of claim 12, wherein the polynucleotide is expressed in the anti-sense orientation.

14. A method of producing a transgenic plant cell comprising introducing into the plant cell a vector comprising a promoter operably linked to a polynucleotide encoding a polypeptide comprising the amino acid sequence from position 220 to position 749 of SEQ ID NO: 2, wherein the polypeptide has cellulose synthase activity.

15. The method of claim 14, wherein the polypeptide comprises SEQ ID NO: 2.

16. The method of claim 14, wherein the polynucleotide comprises the nucleotide sequence from position 660 to position 2250 of SEQ ID NO: 1.

17. The method of claim 15, wherein the polynucleotide comprises the nucleotide sequence from position 69 to position 3005 of SEQ ID NO: 1.

18. The method of claim 14, wherein the polynucleotide comprises SEQ ID NO: 1.

19. The method of claim 17, wherein the polynucleotide is expressed in the anti-sense orientation.

20. The method of claim 16, wherein the polynucleotide is expressed in the anti-sense orientation.

21. A method for producing a transgenic plant comprising introducing into the plant an exogenous polynucleotide encoding a polypeptide comprising the amino acid sequence from position 220 to position 749 of SEQ ID NO: 2, wherein the polypeptide has cellulose synthase activity.

22. A transgenic plant comprising the vector of claim 7.

23. The transgenic plant of claim 22, which is a tree.

24. An isolated polynucleotide encoding a polypeptide comprising the amino acid sequence from position 220 to position 749 of SEQ ID NO: 2, wherein the polypeptide has UDP-glucose binding activity.

25. The polynucleotide of claim 24, wherein the polypeptide comprises SEQ ID NO: 2.

26. The polynucleotide of claim 24, wherein the polynucleotide comprises the nucleotide sequence from position 660 to position 2250 of SEQ ID NO: 1.

* * * * *

UNITED STATES PATENT AND TRADEMARK OFFICE
CERTIFICATE OF CORRECTION

| | | |
|---|---|---|
| PATENT NO. | : 7,049,481 B1 | Page 1 of 1 |
| APPLICATION NO. | : 09/980043 | |
| DATED | : May 23, 2006 | |
| INVENTOR(S) | : Vincent L. Chiang et al. | |

It is certified that error appears in the above-identified patent and that said Letters Patent is hereby corrected as shown below:

Claim 10, line 34, "associated" should be changed to --linked--.

Signed and Sealed this

Eighth Day of May, 2007

JON W. DUDAS
*Director of the United States Patent and Trademark Office*